United States Patent
Rieping et al.

(10) Patent No.: US 7,319,026 B2
(45) Date of Patent: Jan. 15, 2008

(54) AMINO ACID-PRODUCING BACTERIA AND A PROCESS FOR PREPARING L-AMINO ACIDS

(75) Inventors: Mechthild Rieping, Bielefeld (DE); Nicole Siebelt, Rietberg (DE)

(73) Assignee: Degussa AG, Düsseldorf (DE)

( * ) Notice: Subject to any disclaimer, the term of this patent is extended or adjusted under 35 U.S.C. 154(b) by 534 days.

(21) Appl. No.: 10/347,484

(22) Filed: Jan. 21, 2003

(65) Prior Publication Data

US 2004/0082040 A1 Apr. 29, 2004

(30) Foreign Application Priority Data

Mar. 7, 2002 (DE) ............................. 102 10 170
Sep. 25, 2002 (DE) ............................. 102 44 581

(51) Int. Cl.
*C12P 13/08* (2006.01)
*C12N 9/00* (2006.01)
*C12N 1/20* (2006.01)
*C12N 15/00* (2006.01)
*C07H 21/02* (2006.01)

(52) U.S. Cl. .................. 435/115; 435/106; 435/183; 435/252.3; 435/320.1; 536/23.1

(58) Field of Classification Search ................ 435/106, 435/183, 252.3, 320.1, 115; 536/23.1
See application file for complete search history.

(56) References Cited

OTHER PUBLICATIONS

Nagano et al. Biosci Biotechnol Biochem. Sep. 2000;64(9):2012-7.*
Rod et al. J Bacteriol. Aug. 1988;170(8):3601-10.*
Blattner, et al., "The Complete Genome Sequence of *Escherichia coli* K-12," *Science* 277:1453-1462 (1997).
Ivanova, et al., "DNA Base Sequence Variability in *katF* (Putative Sigma Factor) gene of *Escherichia coli*, " *Nucleic Acids Res.* 20:5479-5480 (1992).
Jishage, et al., "Regulation of RNA Polymerase Sigma Subunit Sysnthesis in *Escherichia coli*: Intracellular Levels of Four Species of Sigma Subunit under Various Growth Conditions," *J. Bacteriol.* 178:5447-5451 (1996).
Jishage, et al., "Regulation of RNA Polymerase Sigma Subunit Synthesis in *Escherichia coli*: Intracellular Levels of $\sigma^{70}$ and $\sigma^{38}$." *J. Bacteriol.* 177:6832-6835 (1995).
Jishage, et al., "Variation in RNA Polymerase Sigma Subunit Composition within Different Stocks of *Escherichia coli* W3110," *J. Bacteriol.* 179:959-963 (1997).
Loewen, et al., "Regulation in the *rpoS* Regulon of *Escherichia coli*," *Can. J. Microbiol.* 44:707-717 (1998).
Loewen, et al., "KatF ($\sigma^S$) Synthesis in *Escherichia coli* Is Subject to Posttranscriptional Regulation," *J. Bacteriol* 175:2150-2153 (1993).
Martin, et al., "Selection of tRNA$^{Asp}$ Amber Suppressor Mutants Having Alanine, Arginine, Glutamine, and Lysine Identity," *RNA* 2:919-927 (1996).

Martin, et al., "Genetic Selection for Active *E. coli* Amber tRNA$^{Asn}$ Eclusively Led to Glutamine Inserting Suppressors," *Nucleic Acids Res.* 23:779-784 (1995).
McClain, et al., "Nucleotides that Determine *Escherichia coli* tRNA$^{Arg}$ and tRNA$^{Lys}$ Acceptor Identities Revealed by Analysis of Mutant Opal and Amber Suppressor tRNAs," *Proc. Natl. Sci. USA* 87:9260-9264 (1990).
McClain, et al., "Nucleotides that Contribute to the Identity of *Escherichia colo* tRNA$^{Phe}$," *J. Mol. Biol.* 202:697-709 (1988).
Mulvey, et a., "Nucleotide Sequence of *katF* of *Escherichia coli* Suggests KatF Protein is a Novel σ Transcription Factor," *Nucleic Acids Res.* 17:9979-9991 (1989).
Nagano, et al., "High Expression of the Second Lysine Decarboxylase Gene, *ldc*, in *Escherichia coli* WC196 Due to the Recognition of the Stop Codon (TAG), at a Position Which Corresponds to the 33th Amino Acid Residue of $\sigma^{38}$, as a Serine Residue by the Amber Suppressor, *supD*," *Biosci. Biotechnol. Biochem.* 64:2012-2017 (2000).
Normanly, et al., "Construction of Two *Escherichia coli* Amber Suppressor Genes: tRNA$^{Phe/CUA}$ and tRNA$^{Cys/CUA}$," *Proc. Natl. Acad. Sci. USA* 83:6548-6552 (1986).
Normanly, et al., "Construction of *Escherichia coli* Amber Suppressor tRNA Genes: III. Determination of tRNA Specificity," *J. Mol. Biol.* 213:719-726 (1990).
Komatsoulis, et al., "Recognition of tRNA$^{Cys}$ by *Escherichia coli* Cysteinyl-tRNA Synthetase," *Biochemistry* 32:7435-7444 (1993).
Raftery, et al., "Defined Set of Cloned Termination Suppressors: In Vivo Activity of Isogenetic UAG, UAA, and UGA Suppressor tRNAs," *J. Bacteriol.* 158:849-859 (1984).
Raftery, et al., "Mutation in the D Arm Enables a Suppressor with a CUA Anticodon to Read Both Amber and Ochre Codons in *Escherichia coli*," *J. Mol. Biol.* 190:513-517 (1986).
Raftery, et al., "Systematic Alterations in the Anticodon Arm Make tRNA$^{Glu-Suoc}$ a More Efficient Suppressor," *EMBO J.* 6:1499-1506 (1987).
Schön, et al., "The Selenocysteine-Inserting Opal Suppressor Serine tRNA from *E. coli* Is Highly Unusual in Structure and Modification," *Nucleic Acids Res.* 17:7159-7165 (1989).
Weygand-Duraševič, et al., "Connecting Anticodon Recognition with the Active Site of *Escherichia coli* Glutaminyl-tRNA Synthetase," *J. Mol. Biol.* 240:111-118 (1994).
Yarus, et al., "Construction of a Composite tRNA Gene by Aticodon Loop Transplant," *Proc. Natl. Acad. Sci. USA* 77:5092-5096 (1980).
Database CA 'Online, Chemical Abstracts Service, Columbus, Ohio, US; Kimura, Eiichiro, et al., "Stationary-phase Related Sigma Factor (katF gene) Defect in Microorganism for Enhanced L-Amino Acid Production," retrieved from STN Database accession No. 134:126792 CA, XP-002244384.
Database SWISS-PROT 'Online! 1990, retrieved from SWISS-PROT Database accession No. P13445, XP-002244385.

* cited by examiner

*Primary Examiner*—Tekchand Saidha
*Assistant Examiner*—Christian L. Fronda
(74) *Attorney, Agent, or Firm*—Michael A. Sanzo; Law Office of Michael A. Sanzo, LLC

(57) ABSTRACT

The invention relates to amino acid-producing bacteria from the family Enterobacteriaceae, in particular from the species *Escherichia coli*, which contain a stop codon chosen from the group amber, ochre and opal in the nucleotide sequence for the coding region of the rpoS gene and a suppressor for a stop codon chosen from the group amber suppressor, ochre suppressor and opal suppressor. This invention also relates to a process for preparing amino acids, in particular L-threonine, using these bacteria.

34 Claims, 2 Drawing Sheets

AMINO ACID-PRODUCING BACTERIA AND A PROCESS FOR PREPARING L-AMINO ACIDS

CROSS REFERENCE TO RELATED APPLICATIONS

The present application claims priority under 35 U.S.C. § 119 to German application nos. 102 10 170.1, filed on Mar. 7, 2002 and 102 44 581.8, filed on Sep. 25, 2002, which are incorporated in their entirety herein by reference.

FIELD OF THE INVENTION

The invention relates to amino acid-producing bacteria of the family Enterobacteriaceae, in particular of the species *Escherichia coli*, which contain at least one stop codon chosen from the group comprising amber, ochre and opal in the nucleotide sequence of the coding region of the rpoS gene and the corresponding suppressor for the stop codon chosen from the group amber-suppressor, ochre-suppressor and opal-suppressor. This invention also relates to a process for preparing amino acids, in particular L-threonine, using these bacteria.

PRIOR ART

L-amino acids, in particular L-threonine, are used in human medicine and in the pharmaceutical industry, in the foodstuffs industry and very particularly in animal feedstuffs.

It is known that L-amino acids are prepared by fermentation of strains of Enterobacteriaceae, in particular *Escherichia coli* (*E. coli*) and *Serratia marcescens*. Improvements in the methods of preparation are always being looked for due to the great importance of this process. Process improvements may relate to fermentation technological measures such as e.g. stirring and supplying with oxygen, or the composition of the nutrient media such as e.g. the sugar concentration during fermentation, or working up to the product form by e.g. ion exchange chromatography, or the intrinsic performance characteristics of the microorganism itself.

To improve the performance characteristics of these microorganisms, the methods of mutagenesis, selection and mutant selection are used. In this way strains are obtained that are resistant to antimetabolites such as e.g. the threonine analogon α-amino-β-hydroxyvaleric acid (AHV) or are auxotrophic for important regulatory metabolites and produce L-amino acids such as e.g. L-threonine.

The methods of recombinant DNA engineering have also been used for a number of years for the strain improvement of L-amino acid-producing strains of the family Enterobacteriaceae, by amplifying individual amino acid biosynthesis genes and testing the effect on production.

The rpoS gene, which is also known under the name the katF gene, codes for a protein which is called the $\sigma^{38}$ factor or $\sigma^S$ factor, the $\sigma^{38}$ protein or the $\sigma^{38}$ subunit or else the RpoS protein. The following names for the rpoS gene are also found in the literature, though less commonly: abrD, dpeB, nur, appR, sigS, otsX and snrA. The as factor, as a subunit of RNA-polymerase, controls the expression of a wide variety of different groups of genes (Loewen et al.; Canadian Journal of Microbiology 44 (8): 707-717 (1998)), wherein the regulation mechanisms are often unclear.

Data on the nucleotide sequence of the rpoS or katF gene can be found in Mulvey and Loewen (Nucleic Acids Research 17 (23): 9979-9991 (1989)) and in Blattner et al. (Science 277: 1453-1462 (1997)). Corresponding data can also be found at the National Center for Biotechnology Information (NCBI) of the National Library of Medicine (Bethesda, Md., USA) under the accession numbers X16400 and AE000358. The translation start or the initiation codon for the rpoS gene was determined by Loewen et al. (Journal of Bacteriology 175 (7): 2150-2153 (1993)).

In addition, a number of rpoS alleles are known in strains of *Escherichia coli*, for example in strains of the type in W3110 (Ivanova et al.; Nucleic Acids Research 20 (20): 5479-5480 (1992) and Jishage and Ishihama; Journal of Bacteriology 179 (3): 959-963 (1997)).

In WO 01/05939 it is shown that, after complete switching off of the $\sigma^{38}$ factor by incorporating a deletion in the rpoS gene of a L-glutamic acid producer, glutamic acid production is improved.

Nagano et al. (Bioscience Biotechnology and Biochemistry 64 (9): 2012-2017 (2000)) report on an *Escherichia coli* W3110 strain and the L-lysine producing mutants W196 which both contain a rpoS allele which contains an amber stop codon (TAG) at the point corresponding to position 33 in the amino acid sequence of the $\sigma^{38}$ protein. Strain W196 also contains a mutation in the serU gene coding for L-serine tRNA which is called supD.

DESCRIPTION OF THE INVENTION

Whenever amino acids or L-amino acids are mentioned in the following, this is intended to cover all proteinogenic amino acids with the exception of L-lysine. This means, in particular, L-threonine, L-isoleucine, L-homoserine, L-methionine, L-glutamic acid, L-valine and L-tryptophane, wherein L-threonine is preferred.

"Proteinogenic amino acids" are understood to be those amino acids which are constituents of proteins. These include the amino acids L-glycine, L-alanine, L-valine, L-leucine, L-isoleucine, L-serine, L-threonine, L-cysteine, L-methionine, L-proline, L-phenylalanine, L-tyrosine, L-tryptophane, L-asparagine, L-glutamine, L-aspartic acid, L-glutamic acid, L-arginine, L-lysine, L-histidine and L-selenocysteine.

The invention provides amino acid-producing, in particular L-threonine-producing bacteria from the family Enterobacteriaceae, in particular from the species *Escherichia coli*, which 1) contain at least one stop codon chosen from the group amber, ochre and opal in the nucleotide sequence of the coding region of the rpoS gene and 2) contain the corresponding suppressor for the stop codon, chosen from the group amber suppressor, ochre suppressor and opal suppressor.

The bacteria provided by the present invention can produce amino acids from glucose, saccharose, lactose, fructose, maltose, molasses, optionally starch, optionally cellulose or from glycerine and ethanol. They are representatives of the family Enterobacteriaceae, chosen from the genuses *Escherichia*, *Erwinia*, *Providencia* and *Serratia*. The genuses *Escherichia* and *Serratia* are preferred. In the case of the genus *Escherichia* in particular the species *Escherichia coli* and in the case of the genus *Serratia* in particular the species *Serratia marcescens* are mentioned.

The L-amino acid-producing bacteria provided by the present invention can, inter alia, optionally produce L-lysine as a secondary product in addition to the desired L-amino acid. Bacteria according to the invention produce at most 0 to 40% or 0 to 20%, preferably at most 0 to 10%, particularly preferably at most 0 to 5% of L-lysine compared with the amount of desired L-amino acid. This percentage data corresponds to percentage by weight.

L-threonine-producing strains from the family Enterobacteriaceae preferably possess, inter alia, one or more of the genetic or phenotypical features selected from the group: resistance to α-amino-β-hydroxyvaleric acid, resistance to thialysine, resistance to ethionine, resistance to α-methylserine, resistance to diaminosuccinic acid, resistance to α-aminobutyric acid, resistance to borrelidin, resistance to rifampicin, resistance to valine analogues such as, for example, valine hydroxamate, resistance to purine analogues such as, for example, 6-dimethylaminopurine, a need for L-methionine, optionally partial and compensatable need for L-isoleucine, a need for meso-diaminopimelic acid, auxotrophy with respect to threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally an ability to make use of saccharose, enhancement of the threonine operon, enhancement of homoserine dehydrogenase I-aspartate kinase I preferably the feed-back resistant form, enhancement of homoserine kinase, enhancement of threonine synthase, enhancement of aspartate kinase, optionally the feed-back resistant form, enhancement of aspartate semialdehyd dehydrogenase, enhancement of phosphoenolpyruvate carboxylase, optionally the feed-back resistant form, enhancement of phosphoenolpyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

A stop codon of the amber type is understood to be a stop codon with the base sequence TAG on the coding strand in a DNA molecule corresponding to UAG on the mRNA read by this DNA molecule.

A stop codon of the ochre type is understood to be a stop codon with the base sequence TAA on the coding strand in a DNA molecule corresponding to UAA on the mRNA read by this DNA molecule.

A stop codon of the opal type is understood to be a stop codon with the base sequence TGA on the coding strand in a DNA molecule corresponding to UGA on the mRNA read by this DNA molecule.

The stop codons mentioned are also called nonsense mutations (Edward A. Birge: Bacterial and Bacteriophage Genetics (Third Edition), Springer Verlag, Berlin, Germany, 1994).

The nucleotide sequence for the rpoS gene can be obtained from the prior art. The nucleotide sequence for the rpoS gene corresponding to Accession No. AE000358 is given as SEQ ID NO. 1. The amino acid sequence of the relevant RpoS gene product or protein is given in SEQ ID NO. 2.

The nucleotide sequence for a rpoS allele which contains a stop codon of the amber type at the point in the nucleotide sequence corresponding to position 33 in the amino acid sequence of the RpoS gene product or protein, corresponding to SEQ ID NO. 1 and SEQ ID NO. 2 respectively, is given in SEQ ID NO. 3.

The concentration of $\sigma^{38}$ factor can be determined by the quantitative "Western blot" method as described in Jishage and Ishima (Journal of Bacteriology 177 (23): 6832-6835 (1995)), Jishage et al. (Journal of Bacteriology 178 (18): 5447-5451 (1996)) and Jishage and Ishima (Journal of Bacteriology 179 (3): 959-963 (1997)).

Suppression is generally understood to be the effect whereby the effects of mutation in a "first" gene are compensated for or suppressed by a mutation in a "second" gene. The mutated second gene or second mutation is generally called a suppressor or suppressor gene.

A special case of suppressors relates to alleles of tRNA genes which code for abnormal tRNA molecules which can recognise stop codons so that incorporation of an amino acid takes place instead of chain termination during translation. Extensive explanations of suppression can be found in genetics textbooks such as, for example, the textbook by Rolf Knippers "Molekulare Genetik" (6th edition, Georg Thieme Verlag, Stuttgart, Germany, 1995) or the text book by Ernst-L. Winnacker "Gene und Klone, Eine Einführung in die Gentechnologie" (Dritter, amended reprint, VCH Verlagsgesellschaft, Weinheim, Germany, 1990) or the textbook by F. C. Neidhard (Ed.) "*Escherichia coli* and *Salmonella*, Cellular and Molecular Biology" ($2^{nd}$ Edition, ASM Press, Washington, D.C., USA, 1996).

The suppressors listed in Tables 1, 2 and 3 are, inter alia, tRNA genes or alleles or tRNA suppressors known from the prior art which can suppress stop codons of the amber, ochre or opal type and are thus called amber suppressors, ochre suppressors or opal suppressors. The names for the particular genes or alleles and suppressors were taken from the references cited.

TABLE 1

List of amber suppressors

| Name of the suppressor gene/allele | Name of the tRNA | Amino acid incorporated | Ref. |
| --- | --- | --- | --- |
| supD (=Su1) | Serine tRNA 2 | Ser | 1 |
| supE (=Su2, supY) | Glutamine tRNA2 | Gln | 1 |
| supF | Tyrosine tRNA 1 | Tyr | 1 |
| supP (=Su6) | Leucine tRNA 5 | Leu | 1 |
| supU (=su7) | Tryptophane tRNA | Trp | 1 |
| supZ | Tyrosine tRNA 2 | Tyr | 1 |
| t-RNA$^{Asp}_{CUA}$ | Asp tRNA (CUA) | Lys, Ala, Gln, Arg | 2 |
| tRNAPheCUA | Phenylalanine tRNA | Phe | 3 |
| tRNACysCUA | Cysteine tRNA | Cys | 3 |
| suIII+ amber | Tyrosine tRNA 1 | Tyr | 4 |
| Su$^+$271 | Gln/Trp tRNA | Gln | 5 |
| ARG | Arginine tRNA | Arg, Lys | 6 |
| ARGII | Arginine tRNA | Arg, Gln | 6 |
| LysA20 | Lysine tRNA | Lys | 6 |
| trpT175 | Tryptophane tRNA | Gln | 7 |
| Su79 (=trpT179) | Tryptophane tRNA | Trp | 8 |
| tRNACysCUA | Cysteine tRNA | Cys | 9 |
| t-RNA$^{Asn}_{CUA}$ | Asparagine tRNA | Gln | 10 |
| Ala2 | Alanine tRNA | Ala | 11 |
| Cys | Cysteine tRNA | Lys | 11 |
| ProH | Proline tRNA | Pro | 11 |
| HisA | Histidine tRNA | His | 11 |
| Gly2 | Glycine tRNA | Gly, Gln | 11 |
| Gly1 | Glycine tRNA | Gly | 11 |
| Ile1 | Isoleucine tRNA | Gln, Lys | 11 |
| Met (f) | Methionine tRNA | Lys | 11 |
| Ile2 | Isoleucine tRNA | Lys | 11 |
| AspM | Asparagine tRNA | Lys | 11 |
| Arg | Arginine tNA | Lys, Arg | 11 |
| Thr2 | Threonine tRNA | Lys, Thr | 11 |
| Val | Valine tRNA | Lys, Val | 11 |
| GluA | Glutamic acid tRNA | Glu, Gln, Tyr, Arg | 11 |
| ECF | Phenylalanine tRNA | Phe | 12 |
| ECF9 | Phenylalanine tRNA | Phe | 12 |
| ECF5-2 | Phenylalanine tRNA | Phe, Thr, Tyr | 12 |
| ECF10 | Phenylalanine tRNA | Phe | 12 |
| ECF602 | Phenylalanine tRNA | Phe, Lys, Thr, Val | 12 |
| ECF606 | Phenylalanine tRNA | Phe | 12 |

TABLE 1-continued

List of amber suppressors

| Name of the suppressor gene/allele | Name of the tRNA | Amino acid incorporated | Ref. |
|---|---|---|---|
| ECF11 | Phenylalanine tRNA | Phe | 12 |
| ECF12 | Phenylalanine tRNA | Phe | 12 |
| ECF6 | Phenylalanine tRNA | Phe, Thr | 12 |
| ECF401 | Phenylalanine tRNA | Phe | 12 |
| ECF402 | Phenylalanine tRNA | Phe | 12 |
| ECF403 | Phenylalanine tRNA | Phe | 12 |
| ECF403G45 | Phenylalanine tRNA | Lys | 12 |
| ECF5 | Phenylalanine tRNA | Phe | 12 |
| ECFG73 | Phenylalanine tRNA | Phe, Gln | 12 |

REFERENCES (REF.) FOR TABLE 1

1) Neidhard (Ed.) "*Escherichia coli* and *Salmonella*, Cellular and Molecular Biology" (2nd. Edition, ASM Press, Washington, D.C., USA, 1996)
2) Martin et al, RNA 2 (9): 919-927, 1996
3) Normanly et al, Proceedings of the National Academy of Science USA, 83 (17): 6548-6552, 1986
4) Accession Number K01197
5) Yarus et al, Proceedings of the National Academy of Science USA, 77 (9): 5092-5096, 1990
6) McClain et al, Proceedings of the National Academy of Science USA, 87 (23): 9260-9264, 1990
7) Raftery et al, Journal of Bacteriology 158 (3): 849-859, 1984
8) Raftery et al, Journal of Molecular Biology 190 (3): 513-517, 1986
9) Komatsoulis und Abelson, Biochemistry 32 (29): 7435-7444, 1993
10) Martin et al, Nucleic Acids Research 23(5): 779-784, 1995
11) Normanly et al, Journal of Molecular Biology 213 (4): 719-726, 1990
12) McClain und Foss, Journal of Molecular Biology, 202 (4): 697-709, 1988

TABLE 2

List of ochre suppressors

| Name of the suppressor gene/allele | Name of the tRNA | Amino acid incorporated | Ref. |
|---|---|---|---|
| supB | Glutamine tRNA 1 | Gln | 1 |
| supC | Tyrosine tRNA 1 | Tyr | 1 |
| supD | Serine tRNA 3 | Ser | 1 |
| supG (=supL, supN) | Lysine tRNA | Lys | 1 |
| supM (=supB15) | Tyrosine tRNA 2 | Tyr | 1 |
| supU (=su8) | Tryptophane tRNA | Trp | 1 |
| supV | Tryptophane tRNA | Trp | 1 |
| tRNA$^{Glu}$-Su$_{oc}$205 | Glutamic acid tRNA | Glu | 2 |
| suIII+ ochre | Tyrosine tRNA 1 | Tyr | 3 |
| trpT177 | Tryptophane tRNA | Gln | 4 |
| Su79 (=trpT179) | Tryptophane tRNA | Trp | 5 |

REFERENCES (REF.) FOR TABLE 2

1) Neidhard (Ed.) "*Escherichia coli* and *Salmonella*, Cellular and Molecular Biology" (2nd. Edition, ASM Press, Washington, D.C., USA, 1996)
2) Raftery und Yarus, EMBO Journal 6 (5): 1499-1506, 1987
3) Accession number K01197
4) Raftery et al, Journal of Bacteriology 158 (3): 849-859, 1984
5) Raftery et al, Journal of Molecular Biology 190 (3): 513-517, 1986

TABLE 3

List of opal suppressors

| Name of the suppressor gene/allele | Name of the tRNA | Amino acid incorporated | Ref. |
|---|---|---|---|
| supT | Glycine tRNA 1 | Gly | 1 |
| sumA | Glycine tRNA 2 | Gly | 1 |
| ims, mutA | Glycine tRNA 3 | Gly | 1 |
| supU (=su9) | Tryptophane tRNA | Trp | 1 |
| selC | Serine tRNA | Selenocysteine | 2 |
| GLNA3U70 | Glutamine tRNA | Gln | 3 |
| trpT176 | Tryptophane tRNA | Trp | 4 |
| ARG | Arginine tRNA | Arg | 5 |
| ARGII | Arginine tRNA | Arg | 5 |
| LysA20 | Lysine tRNA | Arg | 5 |

REFERENCES (REF.) FOR TABLE 3

1) Neidhard (Ed.) "*Escherichia coli* and *Salmonella*, Cellular and Molecular Biology" (2nd. Edition, ASM Press, Washington, D.C., USA, 1996)
2) Schon et al, Nucleic Acids Research 17 (18): 7159-7165, 1989
3) Weygand-Durasevic et al, Journal of Molecular Biology 240 (2): 111-118, 1994
4) Raftery et al, Journal of Bacteriology 158 (3): 849-859, 1984
5) McClain et al, Proceedings of the National Academy of Science USA, 87 (23): 9260-9264, 1990

In a first aspect of the invention, it was found that amino acid-, in particular L-threonine-producing bacteria of the species *Escherichia coli* which contain a stop codon chosen from the group amber, ochre and opal in the coding region of the rpoS gene, in particular within the region corresponding to position 2 to 314 of the amino acid sequence of the RpoS protein in accordance with SEQ ID No. 1 and 2 respectively, are further improved in their power to produce amino acids when a suppressor tRNA chosen from the group amber suppressor, ochre suppressor and opal suppressor is incorporated therein.

As a result of the measures according to the invention, the activity or concentration of the RpoS protein or $\sigma^{38}$ factor is lowered in general to >0 to 75%, for example 1 to 75%, to >0 to 50%, for example 0.5 to 50%, to >0 to 25% for example 0.25 to 25%, to >0 to 10%, for example 0.1 to 10%, or to >0 to 5%, for example 0.05 to 5% of the activity or concentration of the wild type protein, or of the activity or concentration of the protein in the initial microogranism. The presence of the suppressor(s) mentioned prevents the activity of the RpoS proteins or $\sigma^{38}$ factor dropping right down to 0.

Accordingly, the invention provides a process for decreasing the intracellular activity or concentration of the RpoS proteins or $\sigma^{38}$ factor in amino acid-producing bacteria of the family Enterobacteriaceae, in particular of the species *Escherichia coli*, wherein in these bacteria 1) at least one stop codon chosen from the group amber, ochre and opal is incorporated in the coding region of the rpoS gene, in particular within the region corresponding to position 2 to 314 of the amino acid sequence of the RpoS protein in accordance with SEQ ID No. 1 or 2, and 2) the corresponding suppressor tRNA gene(s) or allele(s) which code(s) for the suppressor tRNA, chosen from the group amber suppressor, ochre suppressor and opal suppressor, is/are incorporated in these bacteria.

The invention also provides a process for preparing amino acid-producing bacteria of the family Enterobacteriaceae, in particular of the species *Escherichia coli*, wherein in these bacteria 1) a stop codon chosen from the group amber, ochre and opal is incorporated in the coding region of the rpoS gene, in particular within the region corresponding to position 2 to 314 of the amino acid sequence of the RpoS protein in accordance with SEQ ID No. 1 or 2, and that 2) a suppressor tRNA gene or allele which codes for a suppressor tRNA chosen from the group amber suppressor, ochre suppressor and opal suppressor is incorporated in these bacteria.

Finally, the invention provides amino acid-producing bacteria of the family Enterobacteriaceae, in particular of the species *Escherichia coli*, which contain at least one stop codon chosen from the group amber, ochre and opal in the coding region of the rpoS gene, in particular within the region corresponding to position 2 to 314 of the amino acid sequence of the RpoS protein in accordance with SEQ ID No. 1 or 2, and contain the corresponding suppressor tRNA gene or allele which codes for the associated suppressor tRNA, chosen from the group amber suppressor, ochre suppressor and opal suppressor.

With regard to the coding region of the rpoS gene, the following segments have proven to be particularly advantageous for the incorporation of a stop codon chosen from the group amber, ochre and opal, preferably amber:

segment of the coding region between positions 2 and 95, for example position 33, corresponding to the amino acid sequence of the RpoS protein, given in SEQ ID No. 1 or SEQ ID No. 2, segment of the coding region between positions 99 and 168, for example position 148, corresponding to the amino acid sequence of the RpoS protein, given in SEQ ID No. 1 or SEQ ID No. 2, segment of the coding region between positions 190 and 245, corresponding to the amino acid sequence of the RpoS protein, given in SEQ ID No. 1 or SEQ ID No. 2, segment of the coding region between positions 266 and 281, for example position 270 corresponding to the amino acid sequence of the RpoS protein, given in SEQ ID No. 1 or SEQ ID No. 2, and segment of the coding region between positions 287 and 314, for example position 304, corresponding to the amino acid sequence of the RpoS protein, given in SEQ ID No. 1 or SEQ ID No. 2, In the event that the coding region of the rpoS gene has a stop codon of the amber type, an amber suppressor chosen from the group in Table 1 is preferably used.

In the event that the coding region of the rpoS gene has a stop codon of the ochre type, an ochre suppressor chosen from the group in Table 2 is preferably used.

In the event that the coding region of the rpoS gene has a stop codon of the opal type, an opal suppressor chosen from the group in Table 3 is preferably used.

Those amino acid-producing bacteria of the species *Escherichia coli* which are particularly preferred are those which contain a stop codon of the amber type at the point in the nucleotide sequence corresponding to position 33 in the amino acid sequence of the RpoS gene product in accordance with SEQ ID NO. 1 or SEQ ID NO. 2 and preferably contain an amber suppressor chosen from the group in Table 1, in particular the suppressor supE or the suppressor supD, and which produce the amounts of L-lysine, compared with the amount of desired L-amino acid, cited above.

Depending on the suppressor used, the bacteria form a RpoS gene product or $\sigma^{38}$ factor which contains, at position 33 of the amino acid sequence in accordance with SEQ ID NO. 2, instead of L-glutamine, an amino acid chosen from the group L-serine, L-tyrosine, L-leucine, L-tryptophane, L-lysine, L-alanine, L-arginine, L-phenylalanine, L-cysteine, L-proline, L-histidine, L-threonine and L-valine. Thus, for example when using the suppressor supD, L-serine is incorporated instead of L-glutamine. When using suppressors which incorporate the amino acid L-glutamine in position 33 of the RpoS gene product or $\sigma^{38}$ factor, such as for example supE, the amino acid sequence is not altered.

L-threonine-producing bacteria of the species *Escherichia coli* which contain the rpoS allele given in SEQ ID NO. 3 and the suppressor supE given in SEQ ID NO. 4 are very particularly preferred.

The invention also provides, corresponding to this first aspect of the invention, a process for preparing amino acids or amino acid-containing feedstuffs additives in which the following steps are performed:

a) fermentation of bacteria from the family Enterobacteriaceae which contain 1) at least one stop codon chosen from the group amber, ochre and opal, preferably amber, in the coding region of the rpoS gene, in particular within the region corresponding to position 2 to 314 of the amino acid sequence of the RpoS protein in accordance with SEQ ID NO. 1 or 2 and 2) the corresponding suppressor tRNA gene(s) chosen from the group amber suppressor, ochre suppressor and opal suppressor, in a suitable medium, b) enrichment of the amino acid in the fermentation broth, c) isolation of the amino acid or amino acid-containing feedstuffs additive from the fermentation broth, optionally with d) constituents from the fermentation broth and/or the biomass ($\geq 0$ to 100%).

A process for preparing amino acids or amino acid-containing feedstuffs additives is preferred in which Enterobacteriaceae which contain a stop codon of the amber type in the coding region of the rpoS gene corresponding to position 33 of the amino acid sequence of the RpoS protein in accordance with SEQ ID NO. 1 or 2 and an amber suppressor, preferably supE, are fermented in a suitable medium.

The feedstuffs additives according to the invention may be further processed in the liquid and also in the solid form.

Mutations by means of which a stop codon is introduced into the reading frame of the rpoS gene can be produced directly in the relevant host by classical mutagenesis methods using mutagenic substances such as, for example, N-methyl-N'-nitro-N-nitrosoguanidine, or ultraviolet light.

Furthermore, in vitro methods using isolated rpoS DNA such as, for example, treatment with hydroxylamine can be used for mutagenesis (J. H. Miller: A Short Course in Bacterial Genetics, Cold Spring Harbor Laboratory Press, Cold Spring Harbor, 1992). Finally, processes for site-oriented mutagenesis using mutagenic oligonucleotides (T. A. Brown: Gentechnologie für Einsteiger, Spektrum Akademischer Verlag, Heidelberg, 1993) or the polymerase chain reaction (PCR), as is described in the book by Newton and Graham (PCR, Spektrum Akademischer Verlag, Heidelberg, 1994), can be used. The mutations produced can be determined and tested by DNA sequencing, for example using Sanger et al.'s method (Proceedings of the National Academy of Science USA 74 (12): 5463-5467 (1977)).

Suitable mutations can be incorporated into the desired strains with the aid of recombination processes by means of gene or allele replacement. A commonly-used method is the method of gene replacement with the aid of a conditional replicating pSC101 derivate pMAK705, as described by Hamilton et al. (Journal of Bacteriology 171 (9): 4617-4622 (1989)). Other methods described in the prior art such as, for example, the Martinez-Morales et al. method (Journal of Bacteriology 181 (22): 7143-7148 (1999)) or the Boyd et al. method (Journal of Bacteriology 182 (3): 842-847 (2000)) can also be used.

It is also possible to transfer mutations into the desired strains by conjugation or transduction.

Finally, it is possible to use alleles of the rpoS gene known from the prior art which contain a stop codon in the reading frame and introduce these into the desired strains using the methods described above.

The strains obtained in the way described above are preferably mutants, transformants, recombinants, transductants or transconjugants.

In order to produce suppressor mutations in tRNA genes, basically the same methods as described for the rpoS gene can be used. Methods using oligonucleotide engineering, such as were used, for example, by Khorana (Science 203(4381): 614-625 (1979)), can also be used. Furthermore, the tRNA suppressor genes used in the prior art may be used in particular. Methods for searching for, characterising and determining the efficiency of tRNA suppressors are described in the prior art, for example in Miller and Albertini (Journal of Molecular Biology 164 (1): 59-71 (1983)), in McClain and Foss (Journal of Molecular Biology 202 (4): 697-709 (1988)), in Normanly et al. (Journal of Molecular Biology 213 (4): 719-726 (1990)), in Kleina et al. (Journal of Molecular Biology 213: 705-717 (1990)), in Lesley et al. (Promega Notes Magazine 46, p. 02. (1994)) and in Martin et al. (Nucleic Acids Research 23 (5): 779-784 (1995)).

A second aspect of the invention relates to the variant of the RpoS protein given in SEQ ID NO. 6. While working on the present invention, the coding region of this variant of the RpoS protein was identified. This is given in SEQ ID NO. 5.

Accordingly, the invention provides Enterobacteriaceae, in particular those which produce amino acids, which contain or form the RpoS protein given in SEQ ID NO. 6. It is also known that the N-terminal methionine in the proteins formed can be split off by enzymes present in the host.

Furthermore, the invention provides, corresponding to this second aspect, a process for preparing amino acids or amino acid-containing feedstuffs additives, in which the following steps are performed:
a) fermentation of Enterobacteriaceae which contain or form a RpoS protein with the amino acid sequence given in SEQ ID NO. 6,
b) enrichment of the amino acid in the fermentation broth,
c) isolation of the amino acid or amino acid-containing feedstuffs additive from the fermentation broth, optionally with
d) constituents of the fermentation broth and/or the biomass ($\geqq$0 to 100%).

Furthermore, for production of L-threonine with bacteria from the family Enterobacteriaceae, it may be advantageous in addition to incorporating a stop codon in the coding region of the rpoS gene and a corresponding suppressor for a stop codon or in addition to expressing the variant of the RpoS protein given in SEQ ID NO. 6, to enhance one or more enzymes from the known threonine biosynthesis pathway or enzyme(s) for anaplerotic metabolism or enzymes for the production of reduced nicotinamide-adenine-dinucleotide phosphate or enzymes for glycolysis or PTS enzymes or enzymes for sulfur metabolism.

The expression "enhancement" in this connection describes an increase in the intracellular activity or concentration of one or more enzymes or proteins in a microorganism which are coded by the corresponding DNA by, for example, increasing the copy number of the gene or genes, using a strong promoter or a gene which codes for a corresponding enzyme or protein with higher activity and optionally combining these measures.

The use of endogenic genes is generally preferred. "Endogenic genes" or "endogenic nucleotide sequences" are understood to be the genes or nucleotide sequences which are present in the population of a species.

Using the measures of enhancement, in particular overexpression, the activity or concentration of the corresponding protein is generally increased by at least 10%, 25%, 50%, 75%, 100%, 150%, 200%, 300%, 400% or 500%, at most up to 1000% or 2000%, with respect to the wild type protein or the activity or concentration of the protein in the initial microorganism.

Thus, for example, one or more genes, chosen from the following group, may be enhanced, in particular overexpressed:
the thrABC operon coding for aspartate kinase, homoserine dehydrogenase, homoserine kinase and threonine synthase (U.S. Pat. No. 4,278,765),
the pyc gene coding for pyruvate carboxylase (DE-A-19 831 609),
the pps gene coding for phosphoenolpyruvate synthase (Molecular and General Genetics 231 (2):332-336 (1992)),
the ppc gene coding for phosphoenolpyruvate carboxylase (Gene 31: 279-283 (1984)),
the genes pntA and pntB coding for transhydrogenase (European Journal of Biochemistry 158: 647-653 (1986)),
the rhtB gene imparting homoserine resistance (EP-A-0 994 190),
the mqo gene coding for malate:quinone oxidoreductase (DE 100 348 33.5),
the rhtC gene imparting threonine resistance (EP-A-1 013 765),
the thrE gene from *Corynebacterium glutamicum* coding for threonine export protein (DE 100 264 94.8),
the gdhA gene coding for glutamate dehydrogenase (Nucleic Acids Research 11: 5257-5266 (1983); Gene 23: 199-209 (1983)),
the hns gene coding for DNA linkage protein HLP-II (Molecular and General Genetics 212: 199-202 (1988)),
the pgm gene coding for phosphoglucomutase (Journal of Bacteriology 176: 5847-5851 (1994)),
the fba gene coding for fructose biphosphate aldolase (Biochemical Journal 257: 529-534 (1989)),
the ptsI gene from the ptsHIcrr operon, coding for enzyme I in the phosphotransferase system (PTS) (Journal of Biological Chemistry 262: 16241-16253 (1987)),
the ptsH gene from the ptsHIcrr operon, coding for phosphohistidine protein hexose phosphotransferase in the phosphotransferase system (PTS) (Journal of Biological Chemistry 262: 16241-16253 (1987)),
the crr gene from the ptsHIcrr operon, coding for the glucose-specific IIA component in the phosphotransferase system (PTS) (Journal of Biological Chemistry 262: 16241-16253 (1987)), the ptsG gene coding for the glucose-specific IIBC component in the phosphotransferase system (PTS) (Journal of Biological Chemistry 261: 16398-16403 (1986)), the lrp gene coding for the regulator for the leucine regulon (Journal of Biological Chemistry 266: 10768-10774 (1991)), the csrA gene coding for the global regulator (Journal of Bacteriology 175: 4744-4755 (1993)), the fadR gene coding for the regulator for the fad regulon (Nucleic Acids Research 16: 7995-8009 (1988)), the iclR gene coding for the regulator for central intermediary metabolism (Journal of Bacteriology 172: 2642-2649 (1990)), the mopB gene coding for the 10 Kd chaperone (Journal of Biological Chemistry 261: 12414-12419 (1986)), which is also known by the name groES, the ahpC gene from the ahpCF operon, coding for the small subunit in alkyl hydroperoxide reductase (Proceedings of the National Academy of Sciences USA 92: 7617-7621 (1995))

the ahpF gene from the ahpCF operon, coding for the large subunit in alkyl hydroperoxide reductase (Proceedings of the National Academy of Sciences USA 92: 7617-7621 (1995))

the cysK gene coding for cysteine synthase A (Journal of Bacteriology 170: 3150-3157 (1988))

the cysB gene coding for the regulator for the cys regulon (Journal of Biological Chemistry 262: 5999-6005 (1987)), the cysJ gene from the cysJIH operon, coding for flavoprotein in NADPH sulfite reductase (Journal of Biological Chemistry 264: 15796-15808 (1989), Journal of Biological Chemistry 264: 15726-15737 (1989)), the cysH gene from the cysJIH operon, coding for adenylylsulfate reductase (Journal of Biological Chemistry 264: 15796-15808 (1989), Journal of Biological Chemistry 264: 15726-15737 (1989)), and the cysI gene from the cysJIH operon, coding for haemoprotein in NADPH sulfite reductase (Journal of Biological Chemistry 264: 15796-15808 (1989), Journal of Biological Chemistry 264: 15726-15737 (1989)).

Furthermore, it may be advantageous for the production of L-threonine with bacteria from the family Enterobacteriaceae, in addition to incorporating a stop codon in the coding region of the rpoS gene and the corresponding suppressor for the stop codon, or in addition to expressing the variant of the RpoS protein given in SEQ ID NO. 6, to attenuate, in particular to switch off or to reduce the expression of, one or more genes chosen from the following group:

the tdh gene coding for threonine dehydrogenase (Ravnikar und Somerville; Journal of Bacteriology 169: 4716-4721 (1987)), the mdh gene coding for malate dehydrogenase (E.C. 1.1.1.37) (Vogel et al.; Archives in Microbiology 149: 36-42 (1987)), the gene product of the open reading frame (orf) yjfA (Accession Number AAC77180 for the National Center for Biotechnology Information (NCBI, Bethesda, Md., USA)), the gene product of the open reading frame (orf) ytfP (Accession Number AAC77179 for the National Center for Biotechnology Information (NCBI, Bethesda, Md., USA)), the pckA gene coding for the enzyme phosphoenolpyruvate carboxykinase (Medina et al.; Journal of Bacteriology 172: 7151-7156 (1990)), the poxB gene coding for pyruvate oxidase (Grabau und Cronan; Nucleic Acids Research 14 (13): 5449-5460 (1986)), the aceA gene coding for the enzyme isocitrate lyase (Matsuoko und McFadden; Journal of Bacteriology 170: 4528-4536 (1988)), the dgsA gene coding for the DgsA regulator in the phosphotransferase system (Hosono et al.; Bioscience, Biotechnology and Biochemistry 59: 256-261 (1995)), which is also known by the name mlc gene, and the fruR gene coding for fructose repressor (Jahreis et al.; Molecular and General Genetics 226: 332-336 (1991)), which is also known by the name cra gene.

The expression "attenuation" in this connection describes the decrease in or switching off of the intracellular activity or concentration of one or more enzymes or proteins in a microorganism which are coded by the corresponding DNA by, for example, using a weak promoter or a gene or allele which codes for a corresponding enzyme with a low activity or inactivates the corresponding enzyme, protein or gene and optionally combining these measures. Using the measures of attenuation, including decreasing the expression, the activity or concentration of the corresponding protein is generally lowered to 0 to 75%, 0 to 50%, 0 to 25%, 0 to 10% or 0 to 5% of the activity or concentration of the wild type protein, or the activity or concentration of the protein in the initial microorganism.

It has also been demonstrated that in the case of the genes tdh, mdh, pckA, poxB, aceA, dgsA and fruR mentioned above and the open reading frames (ORF) yjfA and ytfP and also for the genes ugpB (gene coding for periplastic linkage protein in the sn-glycerine-3-phosphate transport system), aspA (aspartate ammonium lyase gene (=aspartase gene)), aceB (gene coding for the enzyme malate synthase A) and aceK (gene coding for the enzyme isocitrate dehydrogenase kinase/phosphatase), attenuation can be achieved by 1) incorporating a stop codon, chosen from the group amber, ochre and opal, in the coding region of these genes and 2) simultaneously using a suppressor for the corresponding stop codon, chosen from the group amber suppressor, ochre suppressor and opal suppressor. The use of the stop codon of the amber type and the amber suppressor supE has proven to be particularly advantageous. The methodology described can be transferred to any genes for which attenuation or switching off is intended to be produced.

Microorganisms according to the invention can be cultivated in a batch process, in a fed batch process or in a repeated fed batch process. A review of known cultivation methods is given in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used has to satisfy in an appropriate manner the demands of the particular strains. Descriptions of culture media for different microorganisms are given in the book "Manual of Methods for General Bacteriology" by the American Society for Bacteriology (Washington D.C., USA, 1981).

Sources of carbon which may be used are sugar and carbohydrates such as e.g. glucose, saccharose, lactose, fructose, maltose, molasses, starch and optionally cellulose, oils and fats such as e.g. soy oil, sunflower oil, peanut oil and coconut fat, fatty acids such as e.g. palmitic acid, stearic acid and linoleic acid, alcohols such as e.g. glycerine and ethanol and organic acids such as e.g. acetic acid. These substances may be used individually or as mixtures.

Sources of nitrogen which may be used are organic nitrogen-containing compounds such as peptones, yeast extract, meat extract, malt extract, corn seep liquor, soy bean flour and urea or inorganic compounds such as ammonium sulfate, ammonium chloride, ammonium phosphate, ammonium carbonate and ammonium nitrate. The sources of nitrogen may be used individually or as mixtures.

Sources of phosphorus which may be used are phosphoric acid, potassium dihydrogen phosphate or dipotassium hydrogen phosphate or the corresponding sodium-containing salts. The culture medium must also contain salts of metals, such as e.g. magnesium sulfate or iron sulfate, which are required for growth. Finally essential growth substances such as amino acids and vitamins have to be used in addition to the substances mentioned above. Suitable precursors may also be added to the culture medium. The feedstocks mentioned may be added to the culture in the form of a one-off portion or may be fed in a suitable manner during cultivation.

To control the pH of the culture, basic compounds such as sodium hydroxide, potassium hydroxide, ammonia or ammoniacal water or acid compounds such as phosphoric acid or sulfuric acid are used in an appropriate manner. To control the development of foam, antifoaming agents such as e.g. fatty acid polyglycol esters are used. To maintain stability of the plasmids, suitable selectively acting substances such as e.g. antibiotics may be added to the medium. In order to maintain aerobic conditions, oxygen or oxygen-containing gas mixtures such as e.g. air are introduced into the culture. The temperature of the culture is normally 25° C. to 45° C. and is preferably 30° C. to 40° C. The culture is continued until a maximum of L-amino acids has been formed. This objective is normally achieved within 10 hours to 160 hours.

Analysis of amino acids can be performed using anion exchange chromatography followed by ninhydrin derivatisation, as described in Spackman et al. (Analytical Chemistry 30: 1190-1206 (1958)), or it may be performed using reversed phase HPLC, as described in Lindroth et al. (Analytical Chemistry (1979) 51: 1167-1174).

The following microorganism was deposited as a pure culture on Sep. 9, 2002 at the German Collection of Microorganisms and Cell Cultures (DSMZ, Braunschweig, Germany) in accordance with the Budapest Treaty:
Escherichia coli strain DM1690 as DSM 15189.

Strain DSM 15189 contains a stop codon of the amber type at the point corresponding to position 33 in the amino acid sequence of the RpoS protein and an amber suppressor and produces threonine.

The process according to the invention is used for the fermentative preparation of L-threonine, L-isoleucine, L-methionine, L-homoserine, in particular L-threonine.

The present invention is explained in more detail in the following, making use of working examples.

The minimal (M9) and universal media (LB) for E. coli are described by J. H. Miller (A Short Course in Bacterial Genetics (1992), Cold Spring Harbor Laboratory Press). Isolation of plasmid DNA from E. coli and all techniques relating to restriction and Klenow and alkaline phosphatase treatment are performed as described by Sambrook et al. (Molecular Cloning. A Laboratory Manual (1989), Cold Spring Harbor Laboratory Press). The transformation of E. coli, unless described differently, is performed as described in Chung et al. (Proceedings of the National Academy of Sciences of the United States of America 86: 2172-2175 (1989)). P1 transductions are performed as described by Lengeler et al. (Journal of Bacteriology 124: 26-38 (1975)).

EXAMPLE 1

Transduction of the scr Gene Locus into E. coli K12 Strain MG1655

The scr regulon in the naturally occurring plasmid pUR400 (Schmid et al., Molecular Microbiology 2: 1-8 (1988)) promotes the ability to make use of saccharose as a source of carbon. With the aid of the plasmid pKJL710 (Ulmke et al., Journal of Bacteriology 181: 1920-1923 (1999)), which contains the scr regulon between the two reverse sequence repeats of the transposon Tn1721 (Ubben and Schmitt, Gene 41: 154-152 (1986)), followed by transformation, transposition, conjugation and transduction, the scr regulon can be transferred to the chromosome of Escherichia coli K12. A strain called LJ210 contains the scr regulon integrated in the chromosome at position 6 minutes according to Berlyn-Karte. The bacteriophage P1 is multiplied in this strain and E. coli K12 strain MG1655 (Guyer et al., Cold Spring Harbor Symp., Quant. Biology 45: 135-140 (1981)) is infected with the isolated phage lysate. By plating out on saccharose-containing (2 g/l) minimal medium, MG1655 transductants are obtained which can use saccharose as a source of carbon. A selected clone is given the name MG1655scr.

EXAMPLE 2

In-vivo Mutagenesis of the Strain MG1655scr

Starting from MG1655scr, after incubation at 37° C. in minimal agar to which has been added 2 g/l saccharose and 4 g/l DL-8-hydroxynorvaline (Sigma, Deisenhofen, Germany), spontaneous mutants are isolated which are resistant to the threonine analogon α-amino-β-hydroxyvaleric acid (AHV). A selected mutant is given the name MG1655scrAHVR1.

EXAMPLE 3

Incorporation of a Stop Codon Mutation in the rpoS Gene in MG1655scrAHVR1 by Site-specific Mutagenesis 3.1 Cloning the rpoS Gene from MG1655

The Escherichia coli strain MG1655 is used as donor for chromasomal DNA. A DNA fragment which contains the region of the rpoS gene to be mutated in the middle region is amplified using the polymerase chain reaction (PCR) and synthetic oligonucleotides. Starting from the known sequence of the rpoS gene (Accession Number AE000358, SEQ ID No. 1) for Escherichia coli K12, the following primer oligonucleotides (MWG Biotech, Ebersberg, Germany) are chosen for PCR:

```
rpoS9:                          (SEQ ID No.7)
 5' CAGTTATAGCGGCAGTACC 3' rpoS4:                          (SEQ ID No.8)
 5' GGACAGTGTTAACGACCATTCTC 3'
```

The chromosomal E. coli K12 DNA is isolated in accordance with the manufacturer's data using "Qiagen Genomic-tips 100/G" (Qiagen, Hilden, Germany). A roughly 2 kbp length DNA fragment can be isolated using the specific primers under standard PCR conditions (Innis et al. (1990) PCR Protocols. A Guide to Methods and Applications, Academic Press) with vent polymerase (New England Biolabs GmbH, Frankfurt, Germany).

The amplified DNA fragment is identified using gel electrophoresis in an agarose gel (0.8%) and purified with the QIAquick PCR Purification Kit (Qiagen, Hilden, Germany). The purified PCR product is ligated in accordance with the manufacturer's data using the vector pCR-Blunt II-TOPO (Zero Blunt TOPO PCR Cloning Kit, Invitrogen, Groningen, Holland) and transformed in E. coli strain TOP10 (Invitrogen, Groningen, Holland). Selection of the plasmid-containing cells is performed on LB agar to which has been added 50 mg/l kanamycin. After plasmid DNA isolation, the vector is tested using restriction cleavage and separation in agarose gel (0.8%). The amplified DNA fragment is tested by sequence analysis. The sequence in the PCR product agrees with the sequence given in SEQ ID NO. 9. The plasmid obtained is given the name pCRBluntrpoS9-4.

3.2 Replacing a Glutamine Codon with an Amber Stop Codon by Site-specific Mutagenesis Site-directed mutagenesis is performed with the QuikChange Site-Directed Mutagenesis Kit (Stratagene, La Jolla, USA). The following primer oligonucleotides are chosen for linear amplification:

```
rpoSamber1:                          (SEQ ID No.10)
5' GGCCTTAGTAGAA (TAG) GAACCCAGTGATAACG 3' rpoSamber2:                          (SEQ ID No.11)
5' CGTTATCACTGGGTTC (CTA) TTCTACTAAGGCC 3'
```

These primers are synthesised by MWG Biotech. The amber stop codon which is meant to replace the glutamine at position 33 in the amino acid sequence is labelled with brackets in the nucleotide sequences shown above. The plasmid pCRBluntrpoS9-4 described in example 3.1 is used with each of the two primers complementary to a strand in the plasmid for linear amplification by means of PfuTurbo DNA polymerase. A mutated plasmid with broken circular strands is produced during this elongation of the primer. The product from linear amplification is treated with DpnI. This endonuclease specifically cuts the methylated and semi-methylated template DNA. The newly synthesised broken, mutated vector DNA is transformed in E. coli strain XL1 Blue (Bullock, Fernandez and Short, BioTechniques 5(4) 376379 (1987)). After transformation, the XL1 Blue cells repair the breaks in the mutated plasmids. Selection of the transformants is performed on LB medium with 50 mg/l kanamycin. The plasmid obtained is tested after isolation of the DNA by means of restriction cleavage and separation in agarose gel (0.8%). The DNA sequence of the mutated DNA fragment is tested by sequence analysis. The sequence agrees with the sequence given in SEQ ID NO. 3 in the region of the rpoS gene. The plasmid obtained is given the name pCRBluntrpoSamber.

3.3 Construction of the Replacement Vector pMAK705rpoSamber

The plasmid pCRBluntrpoSamber described in example 3.2 is cleaved with restriction enzymes BamHI and XbaI (Gibco Life Technologies GmbH, Karlsruhe, Germany). After separation in an agarose gel (0.8%) the roughly 2.1 kbp length rpoS fragment containing the mutation is isolated with the QIAquick Gel Extraction Kit (Qiagen, Hilden, Germany). The plasmid pMAK705 described in Hamilton et al. (Journal of Bacteriology 171: 4617-4622 (1989)) is cleaved with restriction enzymes BamHI and XbaT and ligated with the isolated rpoS fragment (T4-DNA-Ligase, Amersham-Pharmacia, Freiburg, Germany). Then the E. coli strain DH5α (Grant et al.; Proceedings of the National Academy of Sciences USA 87: 4645-4649 (1990)) is transformed with the ligation batch (Hanahan, In. DNA Cloning. A Practical Approach. Vol. 1, ILR-Press, Cold Spring Habor, N.Y., 1989). Selection of cells containing the plasmid is performed by plating out the transformation batch on LB agar (Sambrook et al., Molecular Cloning: A Laboratory Manual. $2^{nd}$ Ed., Cold Spring Habor, N.Y., 1989) which is supplemented with 20 mg/l chloramphenicol.

Plasmid DNA is isolated from a transformant using the QIAquick Spin Miniprep Kit from Qiagen and tested by restriction cleavage with the enzymes BamHI, EcoRI, EcoRV, StuI and XbaI followed by agarose gel electrophoresis. The plasmid is given the name pMAK705rpoSamber. A map of the plasmid is shown in FIG. 1.

3.4 Site-specific Mutagenesis of the rpoS Gene E. coli Strain MG1655scrAHVR1

For site-specific mutagenesis of the rpoS gene, the strain MG1655scrAHVR1 described in example 2 is transformed with the plasmid pMAK705rpoSamber. Gene replacement is performed using the selection process described in Hamilton et al. (Journal of Bacteriology 171: 4617-4622 (1989)). Proof that mutation of the rpoSamber allele has taken place in the chromosome is performed using the LightCycler from Roche Diagnostics (Mannheim, Germany). The LightCycler is a combined instrument consisting of a thermocycler and a fluorimeter.

In the first phase, a roughly 0.3 kbp length DNA section which contains the mutation site is amplified by means of PCR (Innis et al., PCR Protocols. A Guide to Methods and Applications, 1990, Academic Press) using the following primer oligonucleotides:

```
rpoSLC1:                          (SEQ ID No.12)
5' CGGAACCAGGCTTTTGCTTG 3' rpoSLC2:                          (SEQ ID No.13)
5' GCGCGACGCGCAAAATAAAC 3'
```

In the second phase the presence of mutation is proven using melting curve analysis (Lay et al.; Clinical Chemistry 43: 2262-2267 (1997)) with two additional oligonucleotides of different lengths and labelled with different fluorescent dyes (LightCycler(LC)-Red640 and fluorescein) which hybridise in the region of the mutation site, using the "Fluorescence Resonance Energy Transfer" method (FRET).

```
rpoSamberC:                          (SEQ ID No.14)
5'LC-Red640-CTTAGTAGAACAGGAACCCAGTG-(P) 3' rpoSamberA:                          (SEQ ID No.15)
5' GATGAGAACGGAGTTGAGGTTTTTGACGAAAAGG-
Fluorescein 3'
```

The primers shown for PCR are synthesised by MWG Biotech (Ebersberg, Germany) and the oligonucleotides for hybridisation are synthesised by TIB MOLBIOL (Berlin, Germany).

In this way, a clone is identified which contains a thymidine base instead of a cytosine base at position 952 in the DNA sequence for the rpoS PCR product (SEQ ID No. 9).

The base triplet thymine adenine guanine is present at position 97-99 of the coding sequence for the rpoS allele (SEQ ID No. 3) and codes for an amber stop codon which leads to termination of translation. This clone is given the name MG1655scrAHVR1rpoS.

EXAMPLE 4

In-Vivo Selection of an Amber Suppressor Mutation in the Strain MG1655scrAHVR1rpoS 4.1 Construction of a Vector with an Amber Stop Codon in the Cat Gene For selection of a suppressor mutation, an amber stop codon is incorporated in the cat gene which codes for chloramphenicol acetyl transferase and imparts resistance to the antibiotic chloramphenicol.

For this purpose, the Cat gene block is ligated in the HindIII linearised vector pTrc99A (both from Pharmacia Biotech, Freiburg, Germany). The *E. coli* strain DH5α (Grant et al.; Proceedings of the National Academy of Sciences USA 87: 4645-4649 (1990)) is transformed with the ligation batch (Hanahan, In. DNA Cloning. A Practical Approach. Vol. 1, ILR-Press, Cold Spring Habor, N.Y., 1989). Selection of cells containing the plasmid is performed by plating out the transformation batch on LB agar (Sambrook et al., Molecular Cloning: A Laboratory Manual. $2^{nd}$ Ed., Cold Spring Habor, N.Y., 1989) which is supplemented with 50 mg/l ampicillin. Plasmid DNA is isolated from a transformant using the QIAquick Spin Miniprep Kit from Qiagen and tested by restriction cleavage followed by agarose gel electrophoresis. The plasmid is given the name pTrc99Acat.

To incorporate an amber stop codon in the coding region of the cat gene, starting from the sequence for the cat gene, primers which contain the cleavage sites for the restriction enzymes AccIII and MscI are synthesised by MWG Biotech, Ebersberg, Germany. The recognition sites for the restriction enzymes are labelled by underscoring in the nucleotide sequences shown below. In the catAccIII primer, behind the AccIII cleavage site, two ATG codons which code for the amino acid methionine at positions 75 and 77 in the cat protein are changed into TAG codons. The amber codons are shown inside brackets in the nucleotide sequences given below.

```
catAccIII:                              (SEQ ID No.16)
5' GCTCATCCGGAATTCCGT (TAG)GCA(TAG)AAAG 3' catMscI:                                (SEQ ID No.17)
5' GTCCATATTGGCCACGTTTAAATC 3'
```

Plasmid DNA from the vector pTrc99Acat is used for PCR. A roughly 300 bp length DNA fragment can be amplified with the specific primers under standard PCR conditions (Innis et al. (1990) PCR Protocols. A Guide to Methods and Applications, Academic Press) using Pfu DNA polymerase (Promega Corporation, Madison, USA). The PCR product is cleaved with the restriction enzymes AccIII and MscI. The vector pTrc99Acat is also digested with the enzymes AccIII and MscI, separated in gel and a 4.7 kbp length fragment is isolated using the QIAquick Gel Extraction Kit. The two fragments are ligated with T4 DNA ligase (Amersham-Pharmacia, Freiburg, Germany). The *E. coli* strain XL1-Blue MRF' (Stratagene, La Jolla, USA) is transformed with the ligation batch and cells containing plasmid are selected on LB agar to which 50 μg/ml ampicillin has been added. Successful cloning can be proven, after plasmid DNA isolation, by control cleavage using the enzymes EcoRI, PvuII, SspI and StyI. The plasmid is given the name pTrc99Acatamber. A map of the plasmid is shown in FIG. 2.

4.2 Selection of Clones with an Amber Suppressor

The strain MG1655scrAHVR1rpoS described in example 3 is transformed with the vectors pTrc99Acat and pTrc99Acatamber. Selection is performed on LB agar which has been supplemented with 20 or 50 μg/ml chioramphenicol. Chloramphenicol-resistant clones which have been transformed with the vector pTrc99Acatamber are transferred to LB Agar to which 50 μg/ml ampicillin has been added, using a toothpick. Plasmid DNA is isolated from chloramphenicol and ampicillin-resistant clones. The vector pTrc99Acatamber is identified by restriction cleavage.

A chloramphenicol-resistant transformant MG1655scrAHVRrpoS/pTrc99Acatamber is cured by the plasmid pTrc99Acatamber by overinoculating several times in LB medium and is given the name DM1690.

4.3 Identification of the Amber Suppressor Mutation in DM1690

4.3.1 Testing for supD Mutation

A known mutation which leads to suppression of amber codons is present in the serU gene which codes for serine tRNA-2. The allele is called supD, the tRNA recognises amber codons and incorporates serine. In the sequence for the supD60 gene (Accession Number M10746) the cytosine adenine adenine anticodon in the wild type serU gene is modified by base replacement to give cytosine thymine adenine and thus recognises uracil adenine guanine codons.

A possible mutation in the chromasomal serU gene can be detected using the LightCycler from Roche Diagnostics (Mannheim, Germany). The LightCycler is a combined instrument consisting of a thermocycler and a fluorimeter.

In the first phase, a roughly 0.3 kbp length DNA section containing the mutation site is amplified by PCR (Innis et al., PCR Protocols. A Guide to Methods and Applications, 1990, Academic Press) using the following primer oligonucleotides:

```
serULC1:                                (SEQ ID No.18)
5' CTTGTACTTTCCAGGGCCAC 3' serULC2:                                (SEQ ID No.19)
5' TTTACCAAAAGCAAGGCGGG 3'
```

In the second phase the presence of mutation is proven using melting curve analysis (Lay et al.; Clinical Chemistry 43: 2262-2267 (1997)) with two additional oligonucleotides of different lengths and labelled with different fluorescent dyes (LightCycler(LC)-Red640 and fluorescein) which hybridise in the region of the mutation site, using the "Fluorescence Resonance Energy Transfer" method (FRET).

```
serUC:                                  (SEQ ID No.20)
5'LC-Red640-TCCGGTTTTCGAGACCGGTC-(P) 3' serUA:                                  (SEQ ID No.21)
5' GAGGGGGATTTGAACCCCCGCTAGAGTTGCCCCTA-
Fluorescein 3'
```

The primers for PCR shown are synthesised by MWG Biotech (Ebersberg, Germany) and the oligonucleotides for the hybridisation shown are synthesised by TIB MOLBIOL (Berlin, Germany).

It can be shown that the wild type serU gene is present in DM1690 and thus there is no supD mutation.

4.3.2 Sequence Analysis of the supE Allele in DM1690

Another known mutation which leads to suppression of amber codons is present in the glnV gene which codes for glutamine tRNA-2. The allele is called supE, the tRNA recognises amber codons and incorporates glutamine. In the sequence for the glnV gene (Accession Number AE000170) the cytosine thymine adenine anticodon in the wild type glnV gene is modified by base replacement to give cytosine thymine adenine and it recognises uracil adenine guanine codons.

Starting from the known sequence for the glnV region of Escherichia coli K12 (Accession Number AE000170), the following primer oligonucleotides (MWG Biotech, Ebersberg, Germany) are chosen for PCR:

```
glnX1:                              (SEQ ID No.22)
5' CTGGCGTGTTGAAACGTCAG 3' glnX2:                              (SEQ ID No.23)
5' CACGCTGTTCGCAACCTAACC 3'
```

The chromosomal DNA from DM1690 used for PCR is isolated in accordance with the manufacturer's data using "Qiagen Genomic-tips 100/G" (Qiagen, Hilden, Germany). A roughly 1 kpb length DNA fragment can be isolated using the specific primers under standard PCR conditions (Innis et al. (1990) PCR Protocols. A Guide to Methods and Applications, Academic Press) with vent polymerase (New England Biolabs GmbH, Frankfurt, Germany). The PCR product is purified with the QIAquick PCR Purification Kit and sequenced by Qiagen Sequencing Services (Qiagen GmbH, Hilden, Germany). The sequence obtained agrees with SEQ ID No. 4 in the region of the glnV gene.

The strain DM1690 possesses the supE allele and suppresses amber codons by incorporating glutamine.

EXAMPLE 5

Preparing L-Threonine Using the Strains MG1655scrAHVR1, MG1655scrAHVR1rpoS and DM1690

The strains MG1655scrAHVR1, MG1655scrAHVR1rpoS and DM1690 are multiplied on minimal medium with the following composition: 3.5 g/l Na2HPO4*2H$_2$O, 1.5 g/l KH2PO4, 1 g/l NH4Cl, 0.1 g/l MgSO4*7H$_2$O, 2 g/l saccharose, 20 g/l agar.

The cultures are incubated for 5 days at 37° C. The formation of L-threonine is monitored in batch cultures of 10 ml which are contained in 100 ml Erlenmeyer flasks. For this purpose, 10 ml of preculture medium with the following composition: 2 g/l yeast extract, 10 g/l (NH4)$_2$SO$_4$, 1 g/l KH2PO4, 0.5 g/l MgSO4*7H$_2$O, 15 g/l CaCO3, 20 g/l saccharose, is inoculated and the mixture is incubated for 16 hours at 37° C. and 180 rpm on an ESR incubator from Kühner AG (Birsfelden, Switzerland). 250 µl portions of this preculture in each case are transferred to 10 ml of production medium (25 g/l (NH4)$_2$SO$_4$, 2 g/l KH2PO4, 1 g/l MgSO4*7H$_2$O, 0.03 g/l FeSO4*7H$_2$O, 0.018 g/l MnSO4*1H$_2$O, 30 g/l CaCO3, 20 g/l saccharose) and incubated for 48 hours at 37° C. After incubation, the optical density (OD) of the culture suspension is determined using a LP2W photometer from Dr. Lange (Berlin, Germany) at a measurement wavelength of 660 nm.

Then the concentration of L-threonine formed is determined in the sterile filtered supernatant liquid using an amino acid analyser from Eppendorf-BioTronik (Hamburg, Germany) by means of ion exchange chromatography and post-column reaction with ninhydrin detection.

Table 4 gives the results of the trial.

TABLE 4

| Strain | OD (660 nm) | L-threonine g/l |
|---|---|---|
| MG1655scrAHVR1 | 5.6 | 2.15 |
| MG1655scrAHVR1rpoS | 5.3 | 2.34 |
| DM1690 | 5.2 | 2.46 |

Figure 1:
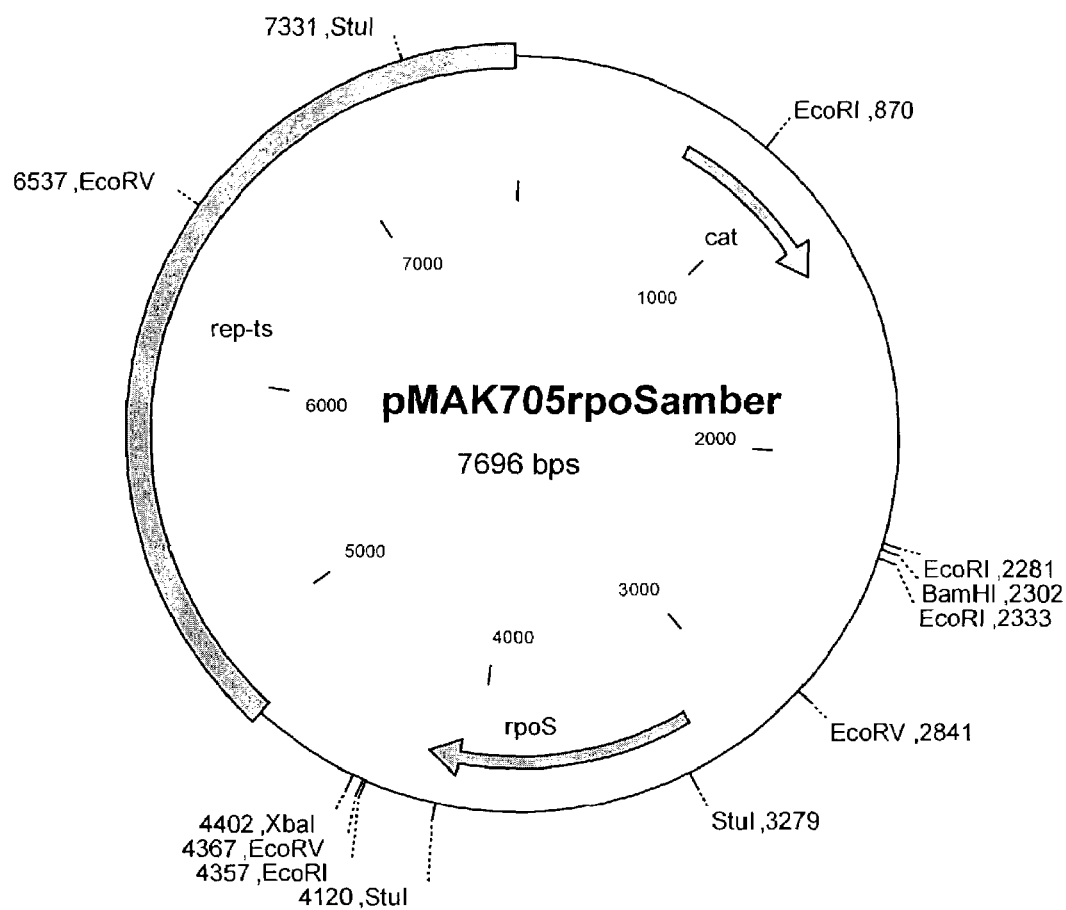
FIG. 1: pMAK705rpoSamber
Figure 2:
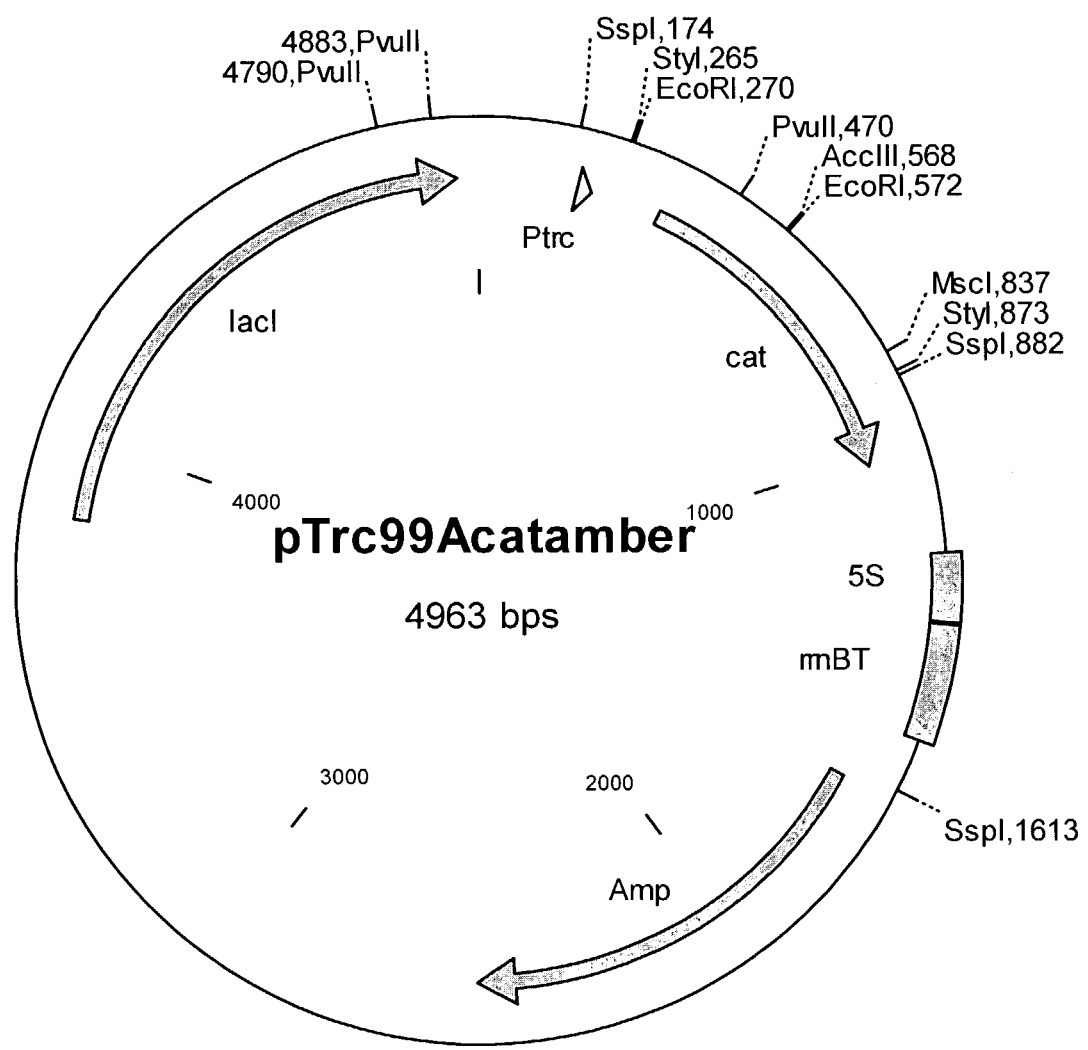
FIG. 2: pTrc99Acatamber

Data relating to length are to be regarded as approximate data. The abbreviations and names used are defined as follows:

| | |
|---|---|
| cat: | Chloramphenicol resistance gene |
| rep-ts: | Temperature-sensitive replication region of the plasmid pSC101 |
| rpoS: | Coding region of the rpoS gene |
| Amp: | Ampicillin resistance gene |
| lacI: | Gene for the repressor gene in the trc promoters |
| Ptrc: | trc promoter region, IPTG-inducible |
| 5S: | 5S rRNA region |
| rrnBT: | rRNA terminator region |

The abbreviations for the restriction enzymes are defined as follows:

| | |
|---|---|
| AccIII: | Restriction endonuclease from Acinetobacter calcoaceticus |
| BamHI: | Restriction endonuclease from Bacillus amyloliquefaciens |
| EcoRI: | Restriction endonuclease from Escherichia coli |
| EcoRV: | Restriction endonuclease from Escherichia coli |
| MscI: | Restriction endonuclease from Microcossus species |
| PvuII: | Restriction endonuclease from Proteus vulgaris |
| SspI: | Restriction endonuclease from Sphaerotilus species |
| StuI: | Restriction endonuclease from Streptomyces tubercidius |
| StyI: | Restriction endonuclease from Salmonella typhi |
| XbaI: | Restriction endonuclease from Xanthomonas badrii |

What is claimed is:

1. An amino acid-producing recombinant bacterium from the Enterobacteriaceae family, wherein said bacterium produces L-threonine and comprises:

(a) at least one stop codon located in the coding region of a nucleotide sequence which codes for the $\sigma^s$ factor having the amino acid sequence of SEQ ID NO:2, wherein said stop codon is selected from the group consisting of: amber; ochre; and opal; and wherein said stop codon lies within the coding region of said nucleotide sequence at a position corresponding to any one of positions 2-314 in the amino acid sequence of the protein of SEQ ID NO:2;

(b) at least one suppressor corresponding to said stop codon and selected from the group consisting of: an amber suppressor; an ochre suppressor; and an opal suppressor; and (c) increased activity of homoserine dehydrogenase compared to an unmodified bacterium from said Enterobacteriaceae family.

2. The recombinant bacterium of claim 1, wherein said bacterium is of the species *Escherichia coli*.

3. The recombinant bacterium of claim 1, wherein said bacterium comprises an amber stop codon and an amber suppressor.

4. The bacterium of claim 3, wherein said amber stop codon lies within the coding region of said nucleotide sequence at a position corresponding to any one of positions 2-95 in the amino acid sequence of the protein of SEQ ID NO:2.

5. The bacterium of claim 4, wherein said amber stop codon lies within the coding region of said nucleotide sequence at a position corresponding to position 33 in the amino acid sequence of the protein of SEQ ID NO:2.

6. The recombinant bacterium of claim 5, wherein said amber stop codon is selected from the group consisting of supD and supE.

7. The recombinant bacterium of claim 6, wherein said bacterium comprises the amber suppressor supE.

8. The recombinant bacterium of claim 1, wherein the amount of L-lysine produced by said bacterium is no more than 40% of the amino acid produced in the greatest amount by said bacterium.

9. The recombinant bacterium of claim 8, wherein the amount of L-lysine produced by said bacterium is no more than 10% of the amino acid produced in the greatest amount by said bacterium.

10. The recombinant bacterium of claim 8, wherein the amount of L-lysine produced by said bacterium is no more than 5% of the amino acid produced in the greatest amount by said bacterium.

11. The recombinant bacterium of any one of claims 1 or 8-10, wherein the amino acid produced in the greatest amount by said bacterium is L-threonine.

12. A recombinant L-threonine-producing bacterium from the Enterobacteriaceae family, wherein said bacterium comprises:
(a) an amber stop codon lying within a nucleotide sequence coding for the protein of SEQ ID NO:2 at a position corresponding to position 33 in the amino acid sequence of the protein of SEQ ID NO:2;
(b) the amber suppressor supE; and
(c) increased activity of homoserine dehydrogenase compared to an unmodified bacterium from the Enterobacteriaceae family.

13. The recombinant bacterium of claim 12, wherein the amino acid produced in the greatest amount by said bacterium is L-threonine.

14. The recombinant bacterium of claim 13, wherein said bacterium is of the species *Escherichia coli*.

15. The recombinant bacterium of any one of claims 12-14, wherein, relative to its wild type counterpart, said bacterium exhibits increased enzymatic activity or concentration of a protein selected from the group consisting of: homoserine kinase; threonine synthase; pyruvate carboxylase; phosphoenolpyruvate synthase; phosphoenolpyruvate carboxylase; transhydrogenase; malate:quinone oxidoreductase; threonine export protein; glutamate dehydrogenase; DNA linkage protein HLP-II; phosphoglucomutase; fructose biphosphate aldolase; enzyme I in the phosphotransferase system; phosphohistidine protein hexose phosphotransferase in the phosphotransferase system; glucose-specific IIA component in the phosphotransferase system; glucose-specific IIBC component in the phosphotransferase system; the regulator in the leucine regulon coded for by the lrp gene; the global regulator coded by the csrA gene; the regulator in the fad regulon coded for by the fadR gene; the regulator in central intermediary metabolism coded for the iclR gene; the 10 Kd chaperone coded for by the mopB gene; the small subunit of alkyl hydroperoxide reductase coded for by the ahpC gene; the large subunit of alkyl hydroperoxide reductase coded for by the ahpF gene; cysteine synthase A; the regulator in the cys regulon coded for by the cysB gene; the flavoprotein in the NADPH sulfite reductase coded for by the cysJ gene; adenylylsulfate reductase coded for by the cysH gene; and the haemoprotein in NADPH sulfite reductase coded for by the cysI gene.

16. The recombinant bacterium of claim 15, wherein, relative to its wild type counterpart, said enzymatic activity or concentration of said protein is increased by at least 50%.

17. The recombinant bacterium of claim 16, wherein, relative to its wild type counterpart, said enzymatic activity or concentration of said protein is increased by at least 100%.

18. The recombinant bacterium of claim 16, wherein, relative to its wild type counterpart, said enzymatic activity or concentration of said protein is increased by at least 300%.

19. The recombinant bacterium of any one of claims 12-14, wherein, relative to its wild type counterpart, said bacterium overexpresses at least one gene selected from the group consisting of: the thrABC operon; the pyc gene; the pps gene; the ppc gene; the pntA gene; the pntB gene; the rhtB gene; the mqo gene; the rhtC gene; the thrE gene; the gdhA gene; the hns gene; the pgm gene; the fba gene; the ptsI gene in the ptsHIcrr operon; the ptsH gene in the ptsHIcrr operon; the crr gene in the ptsHIcrr operon; the ptsG gene; the lrp gene; the csrA gene; the fadR gene; the iclR gene; the mopB gene; the ahpC gene; the ahpF gene; the cysK gene; the cysB gene; the cysJ gene; the cysH gene; and the cysI gene.

20. The recombinant bacterium of claim 19, wherein said nucleotide sequence is overexpressed sufficiently so that the activity of the gene product is increased by at least 50%.

21. The recombinant bacterium of claim 19, wherein said nucleotide sequence is overexpressed sufficiently so that the activity of the gene product is increased by at least 100%.

22. The recombinant bacterium of claim 19, wherein said nucleotide sequence is overexpressed sufficiently so that the activity of the gene product is increased by at least 300%.

23. The recombinant bacterium of any one of claims 12-14, wherein, relative to its wild type counterpart, at least one gene in said bacterium is attenuated, the attenuated gene being selected from the group consisting of: the tdh gene coding for threonine dehydrogenase; the mdh gene coding for malate dehydrogenase; the gene product of the open reading frame yjfA (accession no. AAC77180, NCBI, Bethesda, MD); the gene product of the open reading frame ytfP (accession no. AAC77179, NCBI, Bethesda, MD); the pckA gene coding for phosphoenolpyruvate carboxykinase; the poxB gene coding for pyruvate oxidase; the aceA gene coding for isocytrate lyase; the dgsA gene coding for the DgsA regulator in the phosphotransferase system; and the fruR gene coding for fructose repressor.

24. The recombinant bacterium of claim 23, wherein, relative to said wild type counterpart, said attenuated gene produces a gene product that is decreased in activity or concentration by at least 50%.

25. The recombinant bacterium of claim 23, wherein, relative to said wild type counterpart, said attenuated gene produces a gene product that is decreased in activity or concentration by at least 75%.

26. The amino acid-producing recombinant bacterium of claim 1 wherein said bacterium produces an RpoS protein with the amino acid sequence of SEQ ID NO:2 but where the amino acid at position 33 is selected from the group consisting of: L-serine; L-tyrosine; L-leucine; L-tryptophane; L-lysine; L-alanine; L-arginine; L-phenylalanine; L-cysteine; L-proline; L-histidine; L-threonine; and L-valine.

27. The recombinant bacterium of claim 26, wherein the amino acid produced in the greatest amount by said bacterium is selected from the group consisting of: L-threonine; L-isoleucine; L-homoserine; L-methionine; L-glutamic acid; L-valine; and L-tryptophane.

28. A process for preparing L-threonine, comprising:
(a) fermenting the recombinant bacterium of claim 1 in a fermentation medium;
(b) enriching said selected amino acid in the fermentation medium or recombinant bacterium of step (a); and
(c) preparing an isolated preparation by purifying said selected amino acid from the enriched fermentation medium or recombinant bacterium of step (b).

29. The process of claim 28, wherein said isolated preparation, in addition to said L-threonine comprises biomass or constituents of the fermentation medium.

30. A process for preparing L-threonine, comprising:
(a) fermenting the recombinant bacterium of claim 1 in a fermentation medium, wherein said bacterium comprises:
(i) a stop codon of the amber type lying within the coding region of said nucleotide sequence at a position and corresponding to position 33 in the amino acid sequence of the RpoS protein as shown in SEQ ID NO:2; and
(ii) the amber suppressor supE;
(b) enriching L-threonine in the fermentation medium or recombinant bacterium of step (a); and
(c) preparing an isolated preparation by purifying threonine from the enriched fermentation medium or recombinant bacterium of step (b).

31. The process of claim 30, wherein said isolated preparation, in addition to threonine, comprises biomass or constituents of the fermentation medium.

32. The process of claim 30, wherein said recombinant bacterium is of the species *Escherichia coli.*

33. A bacterium of the species *Escherichia coli* having all the characteristics of strain DM1690, deposited as DSM 15189 at the German Collection of Microorganisms and Cell Cultures (DSMZ, Braunschweig, Germany).

34. The process of any one of claims 30-32, wherein said bacteria have all the characteristics of *E. coli* strain DM1690, deposited as DSM 15189.

\* \* \* \* \*

SEQUENCE LISTING

<160> NUMBER OF SEQ ID NOS: 23

<210> SEQ ID NO 1
<211> LENGTH: 993
<212> TYPE: DNA
<213> ORGANISM: Escherichia coli
<220> FEATURE:
<221> NAME/KEY: CDS
<222> LOCATION: (1)..(990)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | agt | cag | aat | acg | ctg | aaa | gtt | cat | gat | tta | aat | gaa | gat | gcg | gaa | 48 |
| Met | Ser | Gln | Asn | Thr | Leu | Lys | Val | His | Asp | Leu | Asn | Glu | Asp | Ala | Glu | |
| 1 | | | | 5 | | | | | 10 | | | | | 15 | | |
| ttt | gat | gag | aac | gga | gtt | gag | gtt | ttt | gac | gaa | aag | gcc | tta | gta | gaa | 96 |
| Phe | Asp | Glu | Asn | Gly | Val | Glu | Val | Phe | Asp | Glu | Lys | Ala | Leu | Val | Glu | |
| | | | 20 | | | | | 25 | | | | | 30 | | | |
| cag | gaa | ccc | agt | gat | aac | gat | ttg | gcc | gaa | gag | gaa | ctg | tta | tcg | cag | 144 |
| Gln | Glu | Pro | Ser | Asp | Asn | Asp | Leu | Ala | Glu | Glu | Glu | Leu | Leu | Ser | Gln | |
| | | 35 | | | | | 40 | | | | | 45 | | | | |
| gga | gcc | aca | cag | cgt | gtg | ttg | gac | gcg | act | cag | ctt | tac | ctt | ggt | gag | 192 |
| Gly | Ala | Thr | Gln | Arg | Val | Leu | Asp | Ala | Thr | Gln | Leu | Tyr | Leu | Gly | Glu | |
| | 50 | | | | | 55 | | | | | 60 | | | | | |
| att | ggt | tat | tca | cca | ctg | tta | acg | gcc | gaa | gaa | gaa | gtt | tat | ttt | gcg | 240 |
| Ile | Gly | Tyr | Ser | Pro | Leu | Leu | Thr | Ala | Glu | Glu | Glu | Val | Tyr | Phe | Ala | |
| 65 | | | | | 70 | | | | | 75 | | | | | 80 | |
| cgt | cgc | gca | ctg | cgt | gga | gat | gtc | gcc | tct | cgc | cgc | cgg | atg | atc | gag | 288 |
| Arg | Arg | Ala | Leu | Arg | Gly | Asp | Val | Ala | Ser | Arg | Arg | Arg | Met | Ile | Glu | |
| | | | | 85 | | | | | 90 | | | | | 95 | | |
| agt | aac | ttg | cgt | ctg | gtg | gta | aaa | att | gcc | cgc | cgt | tat | ggc | aat | cgt | 336 |
| Ser | Asn | Leu | Arg | Leu | Val | Val | Lys | Ile | Ala | Arg | Arg | Tyr | Gly | Asn | Arg | |
| | | | 100 | | | | | 105 | | | | | 110 | | | |
| ggt | ctg | gcg | ttg | ctg | gac | ctt | atc | gaa | gag | ggc | aac | ctg | ggg | ctg | atc | 384 |
| Gly | Leu | Ala | Leu | Leu | Asp | Leu | Ile | Glu | Glu | Gly | Asn | Leu | Gly | Leu | Ile | |
| | | 115 | | | | | 120 | | | | | 125 | | | | |
| cgc | gcg | gta | gag | aag | ttt | gac | ccg | gaa | cgt | ggt | ttc | cgc | ttc | tca | aca | 432 |
| Arg | Ala | Val | Glu | Lys | Phe | Asp | Pro | Glu | Arg | Gly | Phe | Arg | Phe | Ser | Thr | |
| | 130 | | | | | 135 | | | | | 140 | | | | | |
| tac | gca | acc | tgg | tgg | att | cgc | cag | acg | att | gaa | cgg | gcg | att | atg | aac | 480 |
| Tyr | Ala | Thr | Trp | Trp | Ile | Arg | Gln | Thr | Ile | Glu | Arg | Ala | Ile | Met | Asn | |
| 145 | | | | | 150 | | | | | 155 | | | | | 160 | |
| caa | acc | cgt | act | att | cgt | ttg | ccg | att | cac | atc | gta | aag | gag | ctg | aac | 528 |
| Gln | Thr | Arg | Thr | Ile | Arg | Leu | Pro | Ile | His | Ile | Val | Lys | Glu | Leu | Asn | |
| | | | | 165 | | | | | 170 | | | | | 175 | | |
| gtt | tac | ctg | cga | acc | gca | cgt | gag | ttg | tcc | cat | aag | ctg | gac | cat | gaa | 576 |
| Val | Tyr | Leu | Arg | Thr | Ala | Arg | Glu | Leu | Ser | His | Lys | Leu | Asp | His | Glu | |
| | | | 180 | | | | | 185 | | | | | 190 | | | |
| cca | agt | gcg | gaa | gag | atc | gca | gag | caa | ctg | gat | aag | cca | gtt | gat | gac | 624 |
| Pro | Ser | Ala | Glu | Glu | Ile | Ala | Glu | Gln | Leu | Asp | Lys | Pro | Val | Asp | Asp | |
| | | 195 | | | | | 200 | | | | | 205 | | | | |
| gtc | agc | cgt | atg | ctt | cgt | ctt | aac | gag | cgc | att | acc | tcg | gta | gac | acc | 672 |
| Val | Ser | Arg | Met | Leu | Arg | Leu | Asn | Glu | Arg | Ile | Thr | Ser | Val | Asp | Thr | |
| | 210 | | | | | 215 | | | | | 220 | | | | | |
| ccg | ctg | ggt | ggt | gat | tcc | gaa | aaa | gcg | ttg | ctg | gac | atc | ctg | gcc | gat | 720 |
| Pro | Leu | Gly | Gly | Asp | Ser | Glu | Lys | Ala | Leu | Leu | Asp | Ile | Leu | Ala | Asp | |
| 225 | | | | | 230 | | | | | 235 | | | | | 240 | |
| gaa | aaa | gag | aac | ggt | ccg | gaa | gat | acc | acg | caa | gat | gac | gat | atg | aag | 768 |
| Glu | Lys | Glu | Asn | Gly | Pro | Glu | Asp | Thr | Thr | Gln | Asp | Asp | Asp | Met | Lys | |
| | | | | 245 | | | | | 250 | | | | | 255 | | |

-continued

```
cag agc atc gtc aaa tgg ctg ttc gag ctg aac gcc aaa cag cgt gaa     816
Gln Ser Ile Val Lys Trp Leu Phe Glu Leu Asn Ala Lys Gln Arg Glu
        260                 265                 270 gtg ctg gca cgt cga ttc ggt ttg ctg ggg tac gaa gcg gca aca ctg     864
Val Leu Ala Arg Arg Phe Gly Leu Leu Gly Tyr Glu Ala Ala Thr Leu
    275                 280                 285 gaa gat gta ggt cgt gaa att ggc ctc acc cgt gaa cgt gtt cgc cag     912
Glu Asp Val Gly Arg Glu Ile Gly Leu Thr Arg Glu Arg Val Arg Gln
290                 295                 300 att cag gtt gaa ggc ctg cgc cgt ttg cgc gaa atc ctg caa acg cag     960
Ile Gln Val Glu Gly Leu Arg Arg Leu Arg Glu Ile Leu Gln Thr Gln
305                 310                 315                 320 ggg ctg aat atc gaa gcg ctg ttc cgc gag taa                         993
Gly Leu Asn Ile Glu Ala Leu Phe Arg Glu
            325                 330

<210> SEQ ID NO 2
<211> LENGTH: 330
<212> TYPE: PRT
<213> ORGANISM: Escherichia coli

<400> SEQUENCE: 2

Met Ser Gln Asn Thr Leu Lys Val His Asp Leu Asn Glu Asp Ala Glu
1               5                   10                  15

Phe Asp Glu Asn Gly Val Glu Val Phe Asp Glu Lys Ala Leu Val Glu
            20                  25                  30

Gln Glu Pro Ser Asp Asn Asp Leu Ala Glu Glu Leu Leu Ser Gln
        35                  40                  45

Gly Ala Thr Gln Arg Val Leu Asp Ala Thr Gln Leu Tyr Leu Gly Glu
    50                  55                  60

Ile Gly Tyr Ser Pro Leu Leu Thr Ala Glu Glu Val Tyr Phe Ala
65              70                  75                  80

Arg Arg Ala Leu Arg Gly Asp Val Ala Ser Arg Arg Met Ile Glu
            85                  90                  95

Ser Asn Leu Arg Leu Val Val Lys Ile Ala Arg Arg Tyr Gly Asn Arg
            100                 105                 110

Gly Leu Ala Leu Leu Asp Leu Ile Glu Glu Gly Asn Leu Gly Leu Ile
        115                 120                 125

Arg Ala Val Glu Lys Phe Asp Pro Glu Arg Gly Phe Arg Phe Ser Thr
130                 135                 140

Tyr Ala Thr Trp Trp Ile Arg Gln Thr Ile Glu Arg Ala Ile Met Asn
145                 150                 155                 160

Gln Thr Arg Thr Ile Arg Leu Pro Ile His Ile Val Lys Glu Leu Asn
                165                 170                 175

Val Tyr Leu Arg Thr Ala Arg Glu Leu Ser His Lys Leu Asp His Glu
            180                 185                 190

Pro Ser Ala Glu Glu Ile Ala Glu Gln Leu Asp Lys Pro Val Asp Asp
        195                 200                 205

Val Ser Arg Met Leu Arg Leu Asn Glu Arg Ile Thr Ser Val Asp Thr
    210                 215                 220

Pro Leu Gly Gly Asp Ser Glu Lys Ala Leu Leu Asp Ile Leu Ala Asp
225                 230                 235                 240

Glu Lys Glu Asn Gly Pro Glu Asp Thr Thr Gln Asp Asp Met Lys
            245                 250                 255

Gln Ser Ile Val Lys Trp Leu Phe Glu Leu Asn Ala Lys Gln Arg Glu
        260                 265                 270
```

-continued

```
Val Leu Ala Arg Arg Phe Gly Leu Leu Gly Tyr Glu Ala Ala Thr Leu
            275                 280                 285

Glu Asp Val Gly Arg Glu Ile Gly Leu Thr Arg Glu Arg Val Arg Gln
        290                 295                 300

Ile Gln Val Glu Gly Leu Arg Arg Leu Arg Glu Ile Leu Gln Thr Gln
305                 310                 315                 320

Gly Leu Asn Ile Glu Ala Leu Phe Arg Glu
                325                 330
```

<210> SEQ ID NO 3
<211> LENGTH: 993
<212> TYPE: DNA
<213> ORGANISM: Escherichia coli
<220> FEATURE:
<221> NAME/KEY: Allele
<222> LOCATION: (1)..(990)
<223> OTHER INFORMATION: rpoS-Allele
<220> FEATURE:
<221> NAME/KEY: misc_feature
<222> LOCATION: (97)..(99)
<223> OTHER INFORMATION: amber-codon

<400> SEQUENCE: 3

| | | | | | |
|---|---|---|---|---|---|
| atgagtcaga | atacgctgaa | agttcatgat | ttaaatgaag | atgcggaatt | tgatgagaac | 60 |
| ggagttgagg | tttttgacga | aaaggcctta | gtagaatagg | aacccagtga | taacgatttg | 120 |
| gccgaagagg | aactgttatc | gcagggagcc | acacagcgtg | tgttggacgc | gactcagctt | 180 |
| taccttggtg | agattggtta | ttcaccactg | ttaacgccg  | aagaagaagt | ttattttgcg | 240 |
| cgtcgcgcac | tgcgtggaga | tgtcgcctct | cgccgccgga | tgatcgagag | taacttgcgt | 300 |
| ctggtggtaa | aaattgcccg | ccgttatggc | aatcgtggtc | tggcgttgct | ggaccttatc | 360 |
| gaagagggca | acctggggct | gatccgcgcg | gtagagaagt | ttgacccgga | acgtggtttc | 420 |
| cgcttctcaa | catacgcaac | ctggtggatt | cgccagacga | ttgaacgggc | gattatgaac | 480 |
| caaacccgta | ctattcgttt | gccgattcac | atcgtaaagg | agctgaacgt | ttacctgcga | 540 |
| accgcacgtg | agttgtccca | taagctggac | catgaaccaa | gtgcggaaga | gatcgcagag | 600 |
| caactggata | agccagttga | tgacgtcagc | cgtatgcttc | gtcttaacga | gcgcattacc | 660 |
| tcggtagaca | ccccgctggg | tggtgattcc | gaaaaagcgt | tgctggacat | cctgccgat  | 720 |
| gaaaaagaga | acggtccgga | agataccacg | caagatgacg | atatgaagca | gagcatcgtc | 780 |
| aaatggctgt | tcgagctgaa | cgccaaacag | cgtgaagtgc | tggcacgtcg | attcggtttg | 840 |
| ctggggtacg | aagcggcaac | actggaagat | gtaggtcgtg | aaattggcct | cacccgtgaa | 900 |
| cgtgttcgcc | agattcaggt | tgaaggcctg | cgccgtttgc | gcgaaatcct | gcaaacgcag | 960 |
| gggctgaata | tcgaagcgct | gttccgcgag | taa | | | 993 |

<210> SEQ ID NO 4
<211> LENGTH: 75
<212> TYPE: DNA
<213> ORGANISM: Escherichia coli
<220> FEATURE:
<221> NAME/KEY: tRNA
<222> LOCATION: (1)..(75)
<223> OTHER INFORMATION: supE-Allele

<400> SEQUENCE: 4

| | | | | | |
|---|---|---|---|---|---|
| tggggtatcg | ccaagcggta | aggcaccgga | ttctaattcc | ggcattccga | ggttcgaatc | 60 |
| ctcgtacccc | agcca | | | | | 75 |

```
<210> SEQ ID NO 5
<211> LENGTH: 714
<212> TYPE: DNA
<213> ORGANISM: Escherichia coli
<220> FEATURE:
<221> NAME/KEY: CDS
<222> LOCATION: (1)..(711)
<223> OTHER INFORMATION:

<400> SEQUENCE: 5 atg atc gag agt aac ttg cgt ctg gtg gta aaa att gcc cgc cgt tat        48
Met Ile Glu Ser Asn Leu Arg Leu Val Val Lys Ile Ala Arg Arg Tyr
1               5                   10                  15 ggc aat cgt ggt ctg gcg ttg ctg gac ctt atc gaa gag ggc aac ctg        96
Gly Asn Arg Gly Leu Ala Leu Leu Asp Leu Ile Glu Glu Gly Asn Leu
                20                  25                  30 ggg ctg atc cgc gcg gta gag aag ttt gac ccg gaa cgt ggt ttc cgc       144
Gly Leu Ile Arg Ala Val Glu Lys Phe Asp Pro Glu Arg Gly Phe Arg
            35                  40                  45 ttc tca aca tac gca acc tgg tgg att cgc cag acg att gaa cgg gcg       192
Phe Ser Thr Tyr Ala Thr Trp Trp Ile Arg Gln Thr Ile Glu Arg Ala
        50                  55                  60 att atg aac caa acc cgt act att cgt ttg ccg att cac atc gta aag       240
Ile Met Asn Gln Thr Arg Thr Ile Arg Leu Pro Ile His Ile Val Lys
65                  70                  75                  80 gag ctg aac gtt tac ctg cga acc gca cgt gag ttg tcc cat aag ctg       288
Glu Leu Asn Val Tyr Leu Arg Thr Ala Arg Glu Leu Ser His Lys Leu
                85                  90                  95 gac cat gaa cca agt gcg gaa gag atc gca gag caa ctg gat aag cca       336
Asp His Glu Pro Ser Ala Glu Glu Ile Ala Glu Gln Leu Asp Lys Pro
                100                 105                 110 gtt gat gac gtc agc cgt atg ctt cgt ctt aac gag cgc att acc tcg       384
Val Asp Asp Val Ser Arg Met Leu Arg Leu Asn Glu Arg Ile Thr Ser
            115                 120                 125 gta gac acc ccg ctg ggt ggt gat tcc gaa aaa gcg ttg ctg gac atc       432
Val Asp Thr Pro Leu Gly Gly Asp Ser Glu Lys Ala Leu Leu Asp Ile
        130                 135                 140 ctg gcc gat gaa aaa gag aac ggt ccg gaa gat acc acg caa gat gac       480
Leu Ala Asp Glu Lys Glu Asn Gly Pro Glu Asp Thr Thr Gln Asp Asp
145                 150                 155                 160 gat atg aag cag agc atc gtc aaa tgg ctg ttc gag ctg aac gcc aaa       528
Asp Met Lys Gln Ser Ile Val Lys Trp Leu Phe Glu Leu Asn Ala Lys
                165                 170                 175 cag cgt gaa gtg ctg gca cgt cga ttc ggt ttg ctg ggg tac gaa gcg       576
Gln Arg Glu Val Leu Ala Arg Arg Phe Gly Leu Leu Gly Tyr Glu Ala
                180                 185                 190 gca aca ctg gaa gat gta ggt cgt gaa att ggc ctc acc cgt gaa cgt       624
Ala Thr Leu Glu Asp Val Gly Arg Glu Ile Gly Leu Thr Arg Glu Arg
            195                 200                 205 gtt cgc cag att cag gtt gaa ggc ctg cgc cgt ttg cgc gaa atc ctg       672
Val Arg Gln Ile Gln Val Glu Gly Leu Arg Arg Leu Arg Glu Ile Leu
        210                 215                 220 caa acg cag ggg ctg aat atc gaa gcg ctg ttc cgc gag taa              714
Gln Thr Gln Gly Leu Asn Ile Glu Ala Leu Phe Arg Glu
225                 230                 235

<210> SEQ ID NO 6
<211> LENGTH: 237
<212> TYPE: PRT
<213> ORGANISM: Escherichia coli

<400> SEQUENCE: 6
```

```
Met Ile Glu Ser Asn Leu Arg Leu Val Val Lys Ile Ala Arg Tyr
1               5                   10                  15

Gly Asn Arg Gly Leu Ala Leu Leu Asp Leu Ile Glu Glu Gly Asn Leu
            20                  25                  30

Gly Leu Ile Arg Ala Val Glu Lys Phe Asp Pro Glu Arg Gly Phe Arg
            35                  40                  45

Phe Ser Thr Tyr Ala Thr Trp Trp Ile Arg Gln Thr Ile Glu Arg Ala
    50                  55                  60

Ile Met Asn Gln Thr Arg Thr Ile Arg Leu Pro Ile His Ile Val Lys
65                  70                  75                  80

Glu Leu Asn Val Tyr Leu Arg Thr Ala Arg Glu Leu Ser His Lys Leu
                85                  90                  95

Asp His Glu Pro Ser Ala Glu Glu Ile Ala Glu Gln Leu Asp Lys Pro
            100                 105                 110

Val Asp Asp Val Ser Arg Met Leu Arg Leu Asn Glu Arg Ile Thr Ser
            115                 120                 125

Val Asp Thr Pro Leu Gly Gly Asp Ser Glu Lys Ala Leu Leu Asp Ile
            130                 135                 140

Leu Ala Asp Glu Lys Glu Asn Gly Pro Glu Asp Thr Thr Gln Asp Asp
145                 150                 155                 160

Asp Met Lys Gln Ser Ile Val Lys Trp Leu Phe Glu Leu Asn Ala Lys
                165                 170                 175

Gln Arg Glu Val Leu Ala Arg Arg Phe Gly Leu Leu Gly Tyr Glu Ala
            180                 185                 190

Ala Thr Leu Glu Asp Val Gly Arg Glu Ile Gly Leu Thr Arg Glu Arg
            195                 200                 205

Val Arg Gln Ile Gln Val Glu Gly Leu Arg Arg Leu Arg Glu Ile Leu
            210                 215                 220

Gln Thr Gln Gly Leu Asn Ile Glu Ala Leu Phe Arg Glu
225                 230                 235
```

<210> SEQ ID NO 7
<211> LENGTH: 19
<212> TYPE: DNA
<213> ORGANISM: Escherichia coli

<400> SEQUENCE: 7
cagttatagc ggcagtacc                                              19

<210> SEQ ID NO 8
<211> LENGTH: 23
<212> TYPE: DNA
<213> ORGANISM: Escherichia coli

<400> SEQUENCE: 8
ggacagtgtt aacgaccatt ctc                                         23

<210> SEQ ID NO 9
<211> LENGTH: 2012
<212> TYPE: DNA
<213> ORGANISM: Escherichia coli

<400> SEQUENCE: 9
cagttatagc ggcagtacct ataccgtgaa aaaggcgac acactttct atatcgcctg   60 gattactggc aacgatttcc gtgaccttgc tcagcgcaac aatattcagg caccatacgc  120
gctgaacgtt ggtcagacct tgcaggtggg taatgcttcc ggtacgccaa tcactggcgg  180

-continued

```
aaatgccatt acccaggccg acgcagcaga gcaaggagtt gtgatcaagc ctgcacaaaa      240
ttccaccgtt gctgttgcgt cgcaaccgac aattacgtat tctgagtctt cgggtgaaca      300
gagtgctaac aaaatgttgc cgaacaacaa gccaactgcg accacggtca cagcgcctgt      360
aacggtacca acagcaagca caaccgagcc gactgtcagc agtacatcaa ccagtacgcc      420
tatctccacc tggcgctggc cgactgaggg caaagtgatc gaaacctttg cgcttctga       480 gggggcaac aaggggattg atatcgcagg cagcaaagga caggcaatta tcgcgaccgc       540
agatggccgc gttgtttatg ctggtaacgc gctgcgcggc tacggtaatc tgattatcat      600
caaacataat gatgattacc tgagtgccta cgcccataac gacacaatgc tggtccggga      660
acaacaagaa gttaaggcgg ggcaaaaaat agcgaccatg ggtagcaccg gaaccagttc      720
aacacgcttg cattttgaaa ttcgttacaa ggggaaatcc gtaaaccgc tgcgttattt       780 gccgcagcga taaatcggcg gaaccaggct tttgcttgaa tgttccgtca agggatcacg      840
ggtaggagcc accttatgag tcagaatacg ctgaaagttc atgatttaaa tgaagatgcg      900
gaatttgatg agaacggagt tgaggttttt gacgaaaagg ccttagtaga acaggaaccc      960
agtgataacg atttggccga agaggaactg ttatcgcagg gagccacaca gcgtgtgttg     1020
gacgcgactc agctttacct tggtgagatt ggttattcac cactgttaac ggccgaagaa     1080
gaagtttatt ttgcgcgtcg cgcactgcgt ggagatgtcg cctctcgccg ccggatgatc     1140
gagagtaact gcgtctggt ggtaaaaatt gcccgccgtt atggcaatcg tggtctggcg      1200
ttgctggacc ttatcgaaga gggcaacctg ggctgatcc gcgcggtaga gaagtttgac     1260
ccggaacgtg gtttccgctt ctcaacatac gcaacctggt ggattcgcca gacgattgaa     1320
cgggcgatta tgaaccaaac ccgtactatt cgtttgccga ttcacatcgt aaaggagctg     1380
aacgtttacc tgcgaaccgc acgtgagttg tcccataagc tggaccatga accaagtgcg     1440
gaagagatcg cagagcaact ggataagcca gttgatgacg tcagccgtat gcttcgtctt     1500
aacgagcgca ttacctcggt agacacccg ctgggtggtg attccgaaaa agcgttgctg      1560
gacatcctgg ccgatgaaaa agagaacggt ccggaagata ccacgcaaga tgacgatatg     1620
aagcagagca tcgtcaaatg gctgttcgag ctgaacgcca acagcgtga agtgctggca      1680 cgtcgattcg gtttgctggg gtacgaagcg gcaacactgg aagatgtagg tcgtgaaatt     1740
ggcctcaccc gtgaacgtgt tcgccagatt caggttgaag gcctgcgccg tttgcgcgaa     1800
atcctgcaaa cgcaggggct gaatatcgaa gcgctgttcc gcgagtaagt aagcatctgt     1860
cagaaaggcc agtctcaagc gaggctggcc ttttctgtgc acaataaaag gtccgatgcc     1920
catcggacct ttttattaag gtcaaattac cgcccatacg caccaggtaa ttaagaatcc     1980
ggtaaaaccg agaatggtcg ttaacactgt cc                                    2012
```

<210> SEQ ID NO 10
<211> LENGTH: 31
<212> TYPE: DNA
<213> ORGANISM: Artificial sequence
<220> FEATURE:
<223> OTHER INFORMATION: rpoSamber1, modified Escherichia coli sequence

<400> SEQUENCE: 10

```
ggccttagta gaataggaac ccagtgataa c                                      31
```

<210> SEQ ID NO 11
<211> LENGTH: 31
<212> TYPE: DNA

```
<213> ORGANISM: Artificial sequence
<220> FEATURE:
<223> OTHER INFORMATION: rpoSamber2, modified Escherichia coli sequence

<400> SEQUENCE: 11
gttatcactg ggttcctatt ctactaaggc c                          31

<210> SEQ ID NO 12
<211> LENGTH: 20
<212> TYPE: DNA
<213> ORGANISM: Escherichia coli

<400> SEQUENCE: 12
cggaaccagg cttttgcttg                                       20

<210> SEQ ID NO 13
<211> LENGTH: 20
<212> TYPE: DNA
<213> ORGANISM: Escherichia coli

<400> SEQUENCE: 13
gcgcgacgcg caaaataaac                                       20

<210> SEQ ID NO 14
<211> LENGTH: 23
<212> TYPE: DNA
<213> ORGANISM: Artificial sequence
<220> FEATURE:
<223> OTHER INFORMATION: rpoSamberC, modified Escherichia coli sequence

<400> SEQUENCE: 14
cttagtagaa caggaaccca gtg                                   23

<210> SEQ ID NO 15
<211> LENGTH: 34
<212> TYPE: DNA
<213> ORGANISM: Artificial sequence
<220> FEATURE:
<223> OTHER INFORMATION: rpoSamberA, modified Escherichia coli sequence

<400> SEQUENCE: 15
gatgagaacg gagttgaggt ttttgacgaa aagg                       34

<210> SEQ ID NO 16
<211> LENGTH: 31
<212> TYPE: DNA
<213> ORGANISM: Artificial sequence
<220> FEATURE:
<223> OTHER INFORMATION: catAccIII, modified Escherichia coli sequence

<400> SEQUENCE: 16
gctcatccgg aattccgtta ggcatagaaa g                          31

<210> SEQ ID NO 17
<211> LENGTH: 24
<212> TYPE: DNA
<213> ORGANISM: Artificial sequence
<220> FEATURE:
<223> OTHER INFORMATION: catMscI, modified Escherichia coli sequence

<400> SEQUENCE: 17
gtccatattg gccacgttta aatc                                  24

<210> SEQ ID NO 18
<211> LENGTH: 20
```

-continued

```
<212> TYPE: DNA
<213> ORGANISM: Escherichia coli

<400> SEQUENCE: 18
cttgtacttt ccagggccac                                           20

<210> SEQ ID NO 19
<211> LENGTH: 20
<212> TYPE: DNA
<213> ORGANISM: Escherichia coli

<400> SEQUENCE: 19
tttaggaaaa gcaaggcggg                                           20

<210> SEQ ID NO 20
<211> LENGTH: 20
<212> TYPE: DNA
<213> ORGANISM: Artificial sequence
<220> FEATURE:
<223> OTHER INFORMATION: serUC, modified Escherichia coli sequence

<400> SEQUENCE: 20
tccggttttc gagaccggtc                                           20

<210> SEQ ID NO 21
<211> LENGTH: 35
<212> TYPE: DNA
<213> ORGANISM: Artificial sequence
<220> FEATURE:
<223> OTHER INFORMATION: serUA, modified Escherichia coli sequence

<400> SEQUENCE: 21 gaggggatt tgaaccccg gtagagttgc cccta                            35

<210> SEQ ID NO 22
<211> LENGTH: 20
<212> TYPE: DNA
<213> ORGANISM: Escherichia coli

<400> SEQUENCE: 22
ctggcgtgtt gaaacgtcag                                           20

<210> SEQ ID NO 23
<211> LENGTH: 21
<212> TYPE: DNA
<213> ORGANISM: Escherichia coli

<400> SEQUENCE: 23
cacgctgttc gcaacctaac c                                         21
```